United States Patent
Salman et al.

(10) Patent No.: US 12,402,783 B2
(45) Date of Patent: Sep. 2, 2025

(54) SYSTEMS AND METHODS FOR VARYING STIFFNESS OF AN ENDOSCOPIC INSERTION TUBE

(71) Applicant: EndoChoice, Inc., Alpharetta, GA (US)

(72) Inventors: Golan Salman, Atlit (IL); Igal Shteiman, Kfar Yona (IL); Hadar Schwarcz, Netanya (IL); Jeruham Avron, Haifa (IL); Christopher Stephen, Roswell, GA (US)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 18/450,520

(22) Filed: Aug. 16, 2023

(65) Prior Publication Data

US 2023/0389781 A1 Dec. 7, 2023

Related U.S. Application Data

(63) Continuation of application No. 16/716,057, filed on Dec. 16, 2019, now Pat. No. 11,771,310, which is a
(Continued)

(51) Int. Cl.
*A61B 1/005* (2006.01)
*A61B 1/00* (2006.01)
*A61B 1/12* (2006.01)

(52) U.S. Cl.
CPC ........ *A61B 1/0055* (2013.01); *A61B 1/00078* (2013.01); *A61B 1/0052* (2013.01); *A61B 1/12* (2013.01)

(58) Field of Classification Search
CPC . A61B 1/00078; A61B 1/0052; A61B 1/0055; A61B 1/0058; A61B 1/12;
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Office Action dated Jun. 30, 2016 for U.S. Appl. No. 13/655,120.
(Continued)

*Primary Examiner* — Aaron B Fairchild
(74) *Attorney, Agent, or Firm* — Bookoff McAndrews PLLC

(57) ABSTRACT

The specification describes endoscopes that enable varying stiffness of an insertion portion in an endoscope assembly. In one example, an actuator operates either a spring or a flexible tube to vary stiffness of the insertion portion. In alternative examples, an elliptical wheel arrangement or screw mechanism provides a means to increase stiffness of the insertion portion of an endoscope assembly. In further examples, fluid and gas may be used inside the insertion potion to vary stiffness by varying pressure of the fluid/gas.

21 Claims, 20 Drawing Sheets

Related U.S. Application Data continuation of application No. 14/838,509, filed on Aug. 28, 2015, now Pat. No. 10,542,877.

(60) Provisional application No. 62/066,760, filed on Oct. 21, 2014, provisional application No. 62/043,647, filed on Aug. 29, 2014.

(58) Field of Classification Search
CPC ............ A61B 1/00006; A61B 1/00045; A61B 1/0005; A61B 1/0051; A61B 1/0053; A61B 1/0056; A61B 1/0057
USPC ........................................................ 600/149
See application file for complete search history.

(56) References Cited

U.S. PATENT DOCUMENTS

| | | | |
|---|---|---|---|
| 4,027,697 A | 6/1977 | Bonney | |
| 4,037,588 A | 7/1977 | Heckele | |
| 4,084,401 A | 4/1978 | Belardi | |
| 4,402,313 A | 9/1983 | Yabe | |
| 4,461,282 A | 7/1984 | Ouchi | |
| 4,494,549 A | 1/1985 | Namba | |
| 4,532,918 A | 8/1985 | Wheeler | |
| 4,588,294 A | 5/1986 | Siegmund | |
| 4,641,635 A | 2/1987 | Yabe | |
| 4,649,916 A | 3/1987 | Frimberger | |
| 4,727,859 A | 3/1988 | Lia | |
| 4,764,001 A | 8/1988 | Yokota | |
| 4,790,624 A | 12/1988 | Van Hoye et al. | |
| 4,801,792 A | 1/1989 | Yamasita | |
| 4,815,478 A | 3/1989 | Buchbinder | |
| 4,825,850 A | 5/1989 | Opie | |
| 4,871,229 A * | 10/1989 | Tashiro | A61B 1/0051 |
| | | | 600/920 |
| 4,877,314 A | 10/1989 | Kanamori | |
| 4,902,115 A | 2/1990 | Takahashi | |
| 4,976,522 A | 12/1990 | Igarashi | |
| 4,984,878 A | 1/1991 | Miyano | |
| 5,007,406 A | 4/1991 | Takahashi | |
| 5,014,685 A | 5/1991 | Takahashi | |
| 5,143,085 A | 9/1992 | Wilson | |
| 5,193,525 A | 3/1993 | Silverstein | |
| 5,224,929 A | 7/1993 | Remiszewski | |
| 5,296,971 A | 3/1994 | Mori | |
| 5,359,456 A | 10/1994 | Kikuchi | |
| 5,395,329 A | 3/1995 | Fleischhacker | |
| 5,415,158 A * | 5/1995 | Barthel | A61B 1/0056 |
| | | | 600/149 |
| 5,447,148 A | 9/1995 | Oneda | |
| 5,460,167 A | 10/1995 | Yabe | |
| 5,464,007 A | 11/1995 | Krauter | |
| 5,475,420 A | 12/1995 | Buchin | |
| 5,489,256 A | 2/1996 | Adair | |
| 5,518,501 A | 5/1996 | Oneda | |
| 5,518,502 A | 5/1996 | Kaplan | |
| 5,531,664 A * | 7/1996 | Adachi | A61B 1/0052 |
| | | | 600/152 |
| 5,547,455 A | 8/1996 | McKenna | |
| 5,547,457 A | 8/1996 | Tsuyuki | |
| 5,575,765 A | 11/1996 | Krauter | |
| 5,587,839 A | 12/1996 | Miyano | |
| 5,630,782 A | 5/1997 | Adair | |
| 5,630,798 A | 5/1997 | Beiser | |
| 5,662,588 A | 9/1997 | Iida | |
| 5,674,182 A | 10/1997 | Suzuki | |
| 5,685,821 A | 11/1997 | Pike | |
| 5,685,823 A | 11/1997 | Ito | |
| 5,702,347 A | 12/1997 | Yabe | |
| 5,707,344 A | 1/1998 | Nakazawa | |
| 5,725,474 A | 3/1998 | Yasui | |
| 5,725,476 A | 3/1998 | Yasui | |
| 5,725,477 A | 3/1998 | Yasui | |
| 5,725,478 A | 3/1998 | Saad | |
| 5,777,797 A | 7/1998 | Miyano | |
| 5,782,751 A | 7/1998 | Matsuno | |
| 5,800,341 A | 9/1998 | Mckenna | |
| 5,810,715 A | 9/1998 | Moriyama | |
| 5,810,717 A | 9/1998 | Maeda | |
| 5,810,770 A | 9/1998 | Chin | |
| 5,830,121 A | 11/1998 | Enomoto | |
| 5,836,894 A | 11/1998 | Sarvazyan | |
| 5,860,913 A | 1/1999 | Yamaya | |
| 5,870,234 A | 2/1999 | EbbesmeierneeSchitthof | |
| 5,916,148 A | 6/1999 | Tsuyuki | |
| 5,940,126 A | 8/1999 | Kimura | |
| 6,058,109 A | 5/2000 | Lechleider | |
| 6,095,970 A | 8/2000 | Hidaka | |
| 6,095,971 A | 8/2000 | Takahashi | |
| 6,117,068 A | 9/2000 | Gourley | |
| 6,181,481 B1 | 1/2001 | Yamamoto | |
| 6,196,967 B1 | 3/2001 | Lim | |
| 6,261,226 B1 | 7/2001 | McKenna | |
| 6,277,064 B1 | 8/2001 | Yoon | |
| 6,359,674 B1 | 3/2002 | Horiuchi | |
| 6,375,610 B2 | 4/2002 | Verschuur | |
| 6,402,738 B1 | 6/2002 | Ouchi | |
| 6,419,626 B1 | 7/2002 | Yoon | |
| 6,432,041 B1 * | 8/2002 | Taniguchi | A61B 1/0005 |
| | | | 600/117 |
| 6,476,851 B1 | 11/2002 | Nakamura | |
| 6,520,908 B1 | 2/2003 | Ikeda | |
| 6,636,254 B1 | 10/2003 | Onishi | |
| 6,638,214 B2 | 10/2003 | Akiba | |
| 6,673,012 B2 | 1/2004 | Fujii | |
| 6,690,337 B1 | 2/2004 | Mayer, III | |
| 6,712,760 B2 | 3/2004 | Sano | |
| 6,832,984 B2 | 12/2004 | Stelzer | |
| 6,888,119 B2 | 5/2005 | Iizuka | |
| 6,997,871 B2 | 2/2006 | Sonnenschein | |
| 7,154,378 B1 | 12/2006 | Ertas | |
| 7,435,218 B2 | 10/2008 | Krattiger | |
| 7,621,869 B2 | 11/2009 | Ratnakar | |
| 7,630,148 B1 | 12/2009 | Yang | |
| 7,701,650 B2 | 4/2010 | Lin | |
| 7,713,246 B2 | 5/2010 | Shia | |
| 7,746,572 B2 | 6/2010 | Asami | |
| 7,813,047 B2 | 10/2010 | Wang | |
| 7,828,725 B2 | 11/2010 | Maruyama | |
| 7,918,788 B2 | 4/2011 | Lin | |
| 7,927,272 B2 | 4/2011 | Bayer | |
| 7,967,745 B2 | 6/2011 | Gilad | |
| 7,976,462 B2 | 7/2011 | Wright | |
| 8,064,666 B2 | 11/2011 | Bayer | |
| 8,182,422 B2 | 5/2012 | Bayer | |
| 8,197,399 B2 | 6/2012 | Bayer | |
| 8,235,887 B2 | 8/2012 | Bayer | |
| 8,262,558 B2 | 9/2012 | Sato | |
| 8,287,446 B2 | 10/2012 | Bayer | |
| 8,289,381 B2 | 10/2012 | Bayer | |
| 8,300,325 B2 | 10/2012 | Katahira | |
| 8,310,530 B2 | 11/2012 | Bayer | |
| 8,353,860 B2 | 1/2013 | Boulais | |
| 8,447,132 B1 | 5/2013 | Galil | |
| 8,449,457 B2 | 5/2013 | Alzenfeld | |
| 8,460,182 B2 | 6/2013 | Ouyang | |
| 8,585,584 B2 | 11/2013 | Ratnakar | |
| 8,587,645 B2 | 11/2013 | Bayer | |
| 8,672,836 B2 | 3/2014 | Higgins | |
| 8,715,168 B2 | 5/2014 | Ralnakar | |
| 8,797,392 B2 | 8/2014 | Bayer | |
| 8,872,906 B2 | 10/2014 | Bayer | |
| 8,926,502 B2 | 1/2015 | Levy | |
| 9,044,185 B2 | 6/2015 | Bayer | |
| 9,101,266 B2 | 8/2015 | Levi | |
| 9,101,268 B2 | 8/2015 | Levy | |
| 9,101,287 B2 | 8/2015 | Levy | |
| 9,144,664 B2 | 9/2015 | Jacobsen | |
| 9,289,110 B2 | 3/2016 | Woolford | |
| 9,314,147 B2 | 4/2016 | Levy | |
| 9,320,419 B2 | 4/2016 | Kirma | |
| 2001/0036322 A1 | 11/2001 | Bloomfield | |
| 2001/0037130 A1 * | 11/2001 | Adams | A61B 17/068 |
| | | | 606/220 |

(56) References Cited

U.S. PATENT DOCUMENTS

| | | |
|---|---|---|
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083562 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Bouillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0173694 A1* | 7/2007 | Tsuji ................ A61B 1/0052 600/118 |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229658 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0282167 A1 | 12/2007 | Barenboym |
| 2007/0282358 A1 | 12/2007 | Remiszewski |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0086031 A1 | 4/2008 | Mitsuya |
| 2008/0091065 A1 | 4/2008 | Oshima |
| 2008/0130108 A1 | 6/2008 | Bayer |
| 2008/0151070 A1 | 6/2008 | Shlozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel et al. |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0076332 A1* | 3/2009 | Iwasaki ............ A61B 1/00096 600/168 |
| 2009/0079821 A1 | 3/2009 | Bousquet |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0192357 A1 | 7/2009 | Torii |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |

(56) References Cited

U.S. PATENT DOCUMENTS

| | | |
|---|---|---|
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0280449 A1 | 11/2010 | Alvarez |
| 2010/0296178 A1 | 11/2010 | Genet |
| 2010/0326703 A1 | 12/2010 | Gilad |
| 2010/0331820 A1 | 12/2010 | Prisco |
| 2011/0004058 A1 | 1/2011 | Oneda |
| 2011/0004059 A1 | 1/2011 | Arneson |
| 2011/0021875 A1 | 1/2011 | Macnamara |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0264074 A1 | 10/2011 | Tegg |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0089125 A1 | 4/2012 | Scheibe |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274651 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Steglitz |
| 2013/0317295 A1 | 11/2013 | Morse |
| 2013/0317375 A1 | 11/2013 | Garcia |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0087905 A1 | 3/2015 | Ueda |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0272425 A1 | 10/2015 | Ueda |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 102612337 A | 7/2012 |
| CN | 103346470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |

(56) References Cited

FOREIGN PATENT DOCUMENTS

| | | |
|---|---|---|
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | 60-075025 | 4/1985 |
| JP | H01-148231 A | 6/1989 |
| JP | H05-237056 | 9/1993 |
| JP | H1-014860 A | 1/1998 |
| JP | H1043129 | 2/1998 |
| JP | H10239740 | 9/1998 |
| JP | H11-019030 | 1/1999 |
| JP | 11137512 | 5/1999 |
| JP | 2001-321332 | 11/2001 |
| JP | 2002-253491 A1 | 9/2002 |
| JP | 2003-010105 A | 1/2003 |
| JP | 2003-024270 A | 1/2003 |
| JP | 2005253543 | 9/2005 |
| JP | 2006025888 | 2/2006 |
| JP | 2006068109 | 3/2006 |
| JP | 2009-061173 A | 3/2009 |
| JP | 2010178766 A | 8/2010 |
| JP | 2010-201011 A | 9/2010 |
| JP | 2012-081011 A | 4/2012 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | WO 2014/084135 A1 | 6/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance daled Jul. 15. 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action daled Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action daled Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.

(56) References Cited

OTHER PUBLICATIONS

Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,266.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9,2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action mailed Mar. 20, 2017 for U.S. Appl. No. 14/278,293.
Notice of Allowance dated Mar. 21, 2017 for U.S. Appl. No. 14/549,266.
Office Action dated Mar. 22, 2017 for U.S. Appl. No. 14/705,355.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10. 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
International Search Report for PCT/US2015/47334, mailed on Dec. 28, 2015.
International Search Report for PCT/US14/37004, Sep. 25, 2014.
International Search Report for PCT/US2014/037526, Oct. 16, 2014.
International Search Report for PCT/US14/38094, Nov. 6, 2014.
International Search Report for PCT/US2015/012751, malled on Jun. 26, 2015.
International Search Report for PCT/US2014/58143, mailed on Jan. 21, 2015.
International Search Report for PCT/US2014/071085, mailed on Mar. 27, 2015.
International Search Report for PCT/US2015/027902, mailed on Jul. 23, 2015.
International Search Report for PCT/US2015/012506, mailed on Dec. 11, 2015.
International Search Report for PCT/US2015/29421, mailed on Aug. 7, 2015.
International Search Report for PCT/US2015/28962, mailed on Jul. 28, 2015.
International Search Report for PCT/US2015/41396, malled on Sep. 29, 2015.
International Search Report for PCT/US2015/66486, mailed on Dec. 17, 2015.
International Search Report for PCT/US2015/6548, mailed on Feb. 26, 2016.
Office Action date Feb. 26, 2016 for U.S. Appl. No. 14/274,323.
Office Action dated Feb. 4, 2016 for U.S. Appl. No. 14/271,234.
Japanese Office Action in corresponding Japanese Application No. 2021-179469, dated Nov. 1, 2022 (4 pages).
Japanese Office Action in corresponding Japanese Application No. 2021-179469, dated Jun. 27, 2023 (4 pages).

* cited by examiner

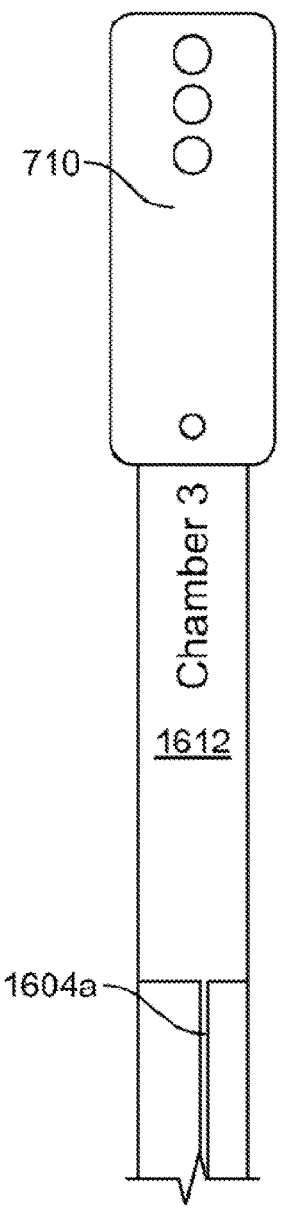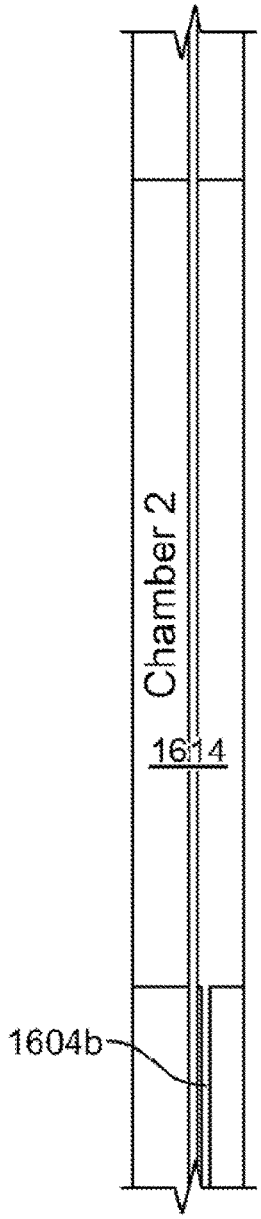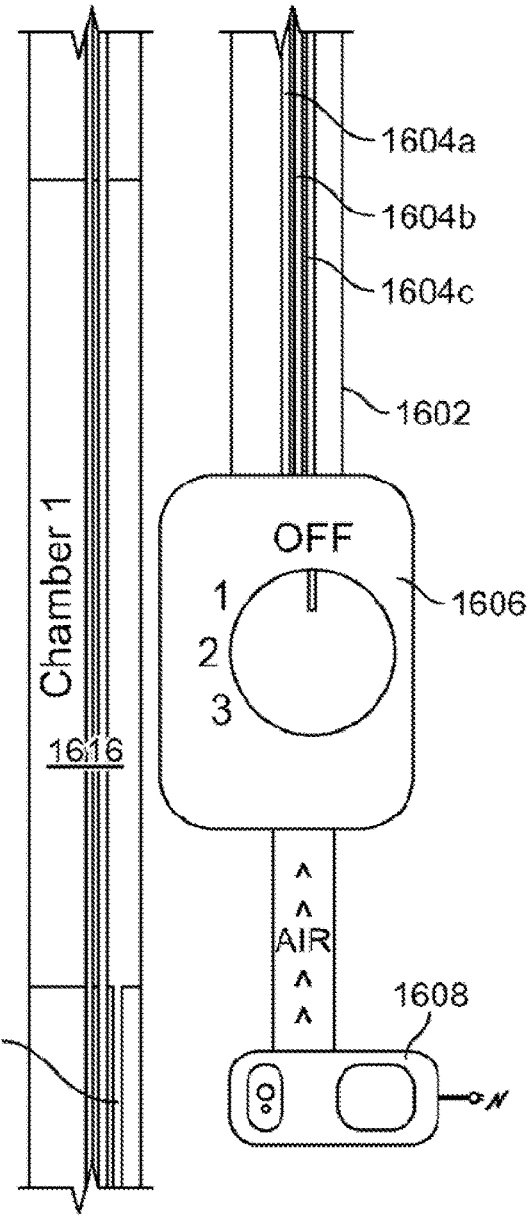
FIG. 16a  FIG. 16b  FIG. 16c  FIG. 16d

SYSTEMS AND METHODS FOR VARYING STIFFNESS OF AN ENDOSCOPIC INSERTION TUBE

CROSS-REFERENCE

This application is a continuation of U.S. Nonprovisional Patent Application No. 16/716,057, filed on Dec. 16, 2019, which is a continuation of U.S. Nonprovisional Patent Application No. 14/838,509, filed on Aug. 28, 2015, which claims the benefit of U.S. Provisional Application No. 62/043,647, filed on Aug. 29, 2014, and U.S. Provisional Application No. 62/066,760, filed on Oct. 21, 2014, for priority. All of the aforementioned applications are herein incorporated by reference in their entirety.

FIELD

The present specification generally relates to an endoscope unit having an insertion portion whereby the stiffness of the insertion portion can be varied.

BACKGROUND

Endoscopes have attained great acceptance within the medical community, since they provide a means to perform procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having one or more video cameras or fiber optic lens assemblies at its distal end. The shaft is connected to a handle, which sometimes includes an ocular for direct viewing. Viewing is also usually possible via an external screen. Various surgical tools may be inserted through a working channel in the endoscope to perform different surgical procedures.

Endoscopes may have a front camera and a side camera to view the internal organ, such as the colon, illuminators for each camera, one or more fluid injectors to clean the camera lens(es) and sometimes also the illuminator(s) and a working channel to insert surgical tools, for example, to remove polyps found in the colon. Often, endoscopes also have fluid injectors ("jet") to clean a body cavity, such as the colon, into which they are inserted. The illuminators commonly used are fiber optics which transmit light, generated remotely, to the endoscope tip section. The use of light-emitting diodes (LEDs) for illumination is also known.

The elongated tubular shaft, also known as the insertion portion of the endoscope has a bending section, proximal to a distal end of the shaft that can bend upon application of an external control to navigate a curved path inside a body cavity, or to access difficult areas within the cavity. However, sometimes it is desirable to vary the degree of bending, based on the application or based on the region inside the body cavity where a distal end of the shaft is navigating. A stiffer insertion portion may reduce the chances of looping of the tubular shaft inside the body cavity, whereas a softer insertion portion may make it easier to reach the cecum. Lack of the ability to vary the stiffness of the insertion portion, such as around the bending portion, could result in patient discomfort and/or increased time for endoscopic examinations. Additionally, some physicians may prefer using a stiffer insertion portion, while some others may prefer a flexible insertion portion. Moreover, repeated reprocessing of parts of endoscope, including its cleaning, may influence the flexible characteristics of the insertion portion. As a result, the insertion portion may become more flexible than required with each time it is cleaned.

U.S. Pat. No. 7,789,827, assigned to Storz, discloses "a flexible endoscope comprising: a flexible shaft portion having a distal and a proximal end and including an outer layer comprising an electrically insulated water-tight material, an inner layer enclosed by said outer layer, a plurality of elongated segments disposed in said outer layer and comprising a polymer material that changes characteristics upon the application of an electrical current, a handle portion coupled to said flexible shaft portion, an electrical source for providing the electrical current to said at least one elongated segment, and electrical conductors electrically connected between said plurality of elongated segments and said electrical source, said electrical conductors extending from said flexible shaft portion through said handle portion to said electrical source, wherein said plurality of elongated segments are positioned in said outer layer in an end-to-end fashion along a longitudinal length of said flexible shaft portion and each elongated segment has at least one end affixed to said inner layer such that upon an application of electrical current to said plurality of elongated segments, said plurality of elongated segments change physical dimension, and wherein said inner layer moves relative to said outer layer based on the dimensional change of at least one of said plurality of elongated segments." However, the '827 patent does not provide a complete mechanical control of the flexibility of the insertion portion.

Thus, what is needed is an insertion portion with an ability to vary its stiffness or flexibility, with minor modifications to the existing structure, shape, size, and manufacturing complexity. Additionally, what is needed is a flexible shaft with an insertion portion that may utilize material available with an endoscope system.

SUMMARY

The following embodiments and aspects thereof are described and illustrated in conjunction with systems, tools and methods, which are meant to be exemplary and illustrative, not limiting in scope.

The present specification discloses various endoscope assemblies comprising an element of variable stiffness embedded within an insertion portion of the endoscope assembly and a controller to vary stiffness of the element.

The present specification discloses an endoscope assembly comprising an insertion portion that is connected to a handle at a proximal end of the insertion portion and a bending portion at a distal end of the insertion portion, comprising: a screw configured to rotate around a longitudinal axis of the endoscope assembly; a housing in physical communication with the screw, wherein the housing is configured to move in a direction that is at least one of a distal direction and a proximal direction along the longitudinal axis of the endoscope assembly, with the rotation of the screw; a stopper placed within the housing; and a wire having a proximal end and a distal end, wherein the proximal end of the wire is connected to the stopper, the wire stretches along a length of the insertion portion, and the distal end of the wire is connected to a proximal end of the bending portion and wherein the wire stiffens the insertion portion upon rotation of the screw towards distal end of the insertion portion.

Optionally, the wire is placed inside a coil fixed to an internal periphery of the insertion portion.

Optionally, the endoscope assembly further comprises a housing containing at least one of the screw, the internal housing, the stopper, and the wire.

Optionally, the endoscope assembly further comprises a knob located in the handle and in physical communication with the screw, wherein a rotation of the knob causes a rotation of the screw.

The stopper may be configured within said housing such that a proximal movement of the housing causes said stopper to move proximally and such that a distal movement of the housing causes the stopper to move distally.

Movement of the wire may cause at least one of the pitch, degree of expansion, degree of compression, and flexibility of the coil to change.

Movement of the wire may cause at least one of the tensile strength, flexibility, or compressibility of the bending portion to change.

Optionally, the housing is positioned around the longitudinal axis of the screw and is configured to move longitudinally along said axis.

The present specification also discloses an endoscope assembly comprising an insertion portion that is connected to a handle at a proximal end of the insertion portion and a bending portion at a distal end of the insertion portion, comprising: an actuator; a spring, having a proximal end and a distal end, wherein the proximal end of the spring is connected to the actuator and wherein the actuator activates the spring; and, a wire, having a proximal end and a distal end, with the proximal end of the wire connected to the distal end of the spring, wherein the wire stretches along a length of the insertion portion and wherein the distal end of the wire is connected to a proximal end of the bending portion, and wherein the wire stiffens the insertion portion upon activation of the spring.

The spring may comprise superelastic material. Optionally, the superelastic material is Nitinol.

Optionally, the actuator is connected to an electric current source that activates the spring. Optionally, the actuator is connected to a heat source that activates the spring. Still optionally, the actuator is connected to a gear motor that activates the spring.

Optionally, the endoscope assembly further comprises a shaft connecting the spring and the wire. The shaft may have a U-shaped structure comprising: a first wall connected to distal end of the spring; and a second wall, parallel to the first wall, connected to the proximal end of the wire.

The wire may be placed inside a coil fixed to an internal periphery of the insertion portion.

Optionally, the endoscope assembly further comprises a housing containing at least one of the actuator, the spring, and the wire.

The present specification also discloses an endoscope assembly comprising an insertion portion that is connected to a handle at a proximal end of the insertion portion and a bending portion at a distal end of the insertion portion, comprising: an actuator; a tube with slits centered and stretching along its longitudinal axis across a portion of its length, the tube having a proximal end and a distal end, wherein the proximal end of the tube is connected to the actuator, and wherein the actuator activates the tube; and, a wire, having a proximal end and a distal end, the proximal end of the wire connected to the tube, wherein the wire stretches along a length of the insertion portion and the distal end of the wire is connected to a proximal end of the bending portion, wherein the wire stiffens the insertion portion upon activation of the tube.

The tube may be manufactured with a superelastic material. Optionally, the superelastic material is Nitinol.

The present specification also discloses an endoscope assembly comprising an insertion portion that is connected to a handle at a proximal end of the insertion portion and a bending portion at a distal end of the insertion portion, comprising: a wheel, approximately shaped as an ellipse, wherein said wheel further comprises a first portion, a second portion, and a center portion; a shaft connected to a center of the wheel; a lever connected to the shaft, wherein rotation of the lever rotates the shaft and the wheel; a wire having a proximal end and a distal end, wherein the proximal end of the wire rests on an edge of the wheel, the wire stretches along a length of the insertion portion and the distal end of the wire is connected to a proximal end of the bending portion and wherein the wire stiffens the insertion portion upon rotation of the wheel; and a stopper connected to the proximal end of the wire, wherein the stopper anchors the wire with the wheel.

Optionally, the wire is placed inside a coil fixed to an internal periphery of the insertion portion.

The present specification also discloses an endoscope assembly comprising a working channel, wherein the outer periphery of the working channel is covered with an enforcement layer providing stiffness to the working channel.

Optionally, the enforcement layer is manufactured from a material comprising at least one metal from family of stainless steel metals.

The present specification also discloses an insertion portion in an endoscope assembly, comprising: at least one flexible tube extending from a proximal end of the insertion portion along length of the insertion portion; a pressure pump connected to the at least one flexible tube at the proximal end of the insertion portion; and a fluid inflating the at least one flexible tube, wherein a pressure of the fluid is controlled by the pressure pump.

Optionally, the fluid is at least one of water, a fluid that changes viscosity based on an applied electric field, a fluid that changes viscosity based on shear rate or shear rate history, a fluid that changes viscosity based on a magnetic field, and a fluid that changes viscosity based on exposure to light.

The fluid may be water sourced from a water supply of the endoscope assembly.

Optionally, varying an operating voltage of the pressure pump controls pressure of the fluid.

A pressure regulator may be connected to the pressure pump to control pressure of the fluid.

Optionally, the at least one flexible tube extending from a proximal end of the insertion portion extends up to a proximal end of bending section of the insertion portion and not into a tip section of the endoscope assembly.

Optionally, the at least one flexible tube extending from a proximal end of the insertion portion extends up to a distal end of the insertion portion.

Still optionally, the at least one flexible tube extending from a proximal end of the insertion portion extends up to an opposite end of the flexible tube, wherein the opposite end is sealed.

The pressure pump may control pressure of the fluid to control flexibility of the at least one flexible tube.

The present specification also discloses an insertion portion in an endoscope assembly, comprising: a flexible tube coiled around an outer circumferential surface of a treatment tool insertion channel embedded inside the insertion portion, the coiled tube extending from a proximal end of the insertion portion along a length of the insertion portion; a pressure pump connected to the flexible tube at the proximal end of the insertion portion; and a fluid inflating the flexible tube, wherein a pressure of the fluid is controlled by the pressure pump.

Optionally, the fluid is at least one of water, a fluid that changes viscosity based on an applied electric field, a fluid that changes viscosity based on shear rate or shear rate history, a fluid that changes viscosity based on a magnetic field, and a fluid that changes viscosity based on exposure to light.

The fluid may be water sourced from a water supply of the endoscope assembly.

Optionally, varying an operating voltage of the pressure pump controls pressure of the fluid.

A pressure regulator may be connected to the pressure pump to control pressure of the fluid.

Optionally, the flexible tube extending from a proximal end of the insertion portion extends up to a proximal end of bending section of the insertion portion and not into said tip section.

Optionally, the flexible tube extending from a proximal end of the insertion portion extends only up to a distal end of the insertion portion.

Still optionally, the flexible tube extending from proximal end of the insertion portion extends up to an opposite end of the flexible tube, wherein the opposite end is sealed.

The pressure pump may control pressure of the fluid to control flexibility of the flexible tube.

The present specification also discloses an insertion portion in an endoscope assembly, comprising: at least one flexible lining stretching along an inner wall of the insertion portion, the flexible lining forming a parallel wall inside the insertion portion such that a gap exists between the parallel wall and the inner wall of the insertion portion, and extending from a proximal end of the insertion portion along a length of the insertion portion; a pressure pump connected to the gap at the proximal end of the insertion portion; and a fluid filling the gap, wherein a pressure of the fluid is controlled by the pressure pump.

The present specification also discloses an insertion portion in an endoscope assembly, comprising: at least one flexible tube extending from a proximal end of the insertion portion along a length of the insertion portion, wherein the flexible tube encloses a gas; at least one sealed chamber into which the at least one flexible tube opens and carries gas into the at least one sealed chamber; and a pressure pump connected to the at least one flexible tube at the proximal end of the insertion portion, wherein a pressure of gas is controlled by the pressure pump.

Optionally, the gas is air.

Optionally, three flexible tubes open into three corresponding sealed chambers.

Each chamber may be located adjacent to one another along a longitudinal axis of the insertion portion.

Each chamber may be concentrically located along a longitudinal axis of the insertion portion.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 16a shows a longitudinal cross-sectional view of a portion of an elongated shaft in an endoscope in accordance with another embodiment;

FIG. 16b shows a longitudinal cross-sectional view of a portion of an elongated shaft in an endoscope in accordance with another embodiment;

FIG. 16c shows a longitudinal cross-sectional view of a portion of an elongated shaft in an endoscope in accordance with another embodiment; and FIG. 16d shows a longitudinal cross-sectional view of a portion of an elongated shaft in an endoscope in accordance with another embodiment.

DETAILED DESCRIPTION

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

It is noted that the term "endoscope" as mentioned to herein may refer particularly to a colonoscope and a gastroscope, according to some embodiments, but is not limited only to colonoscopes and/or gastroscopes. The term "endoscope" may refer to any instrument used to examine the interior of a hollow organ or cavity of the body, provided it further includes an insertion section, bending portion, and viewing tip as described herein.

Figure 1:
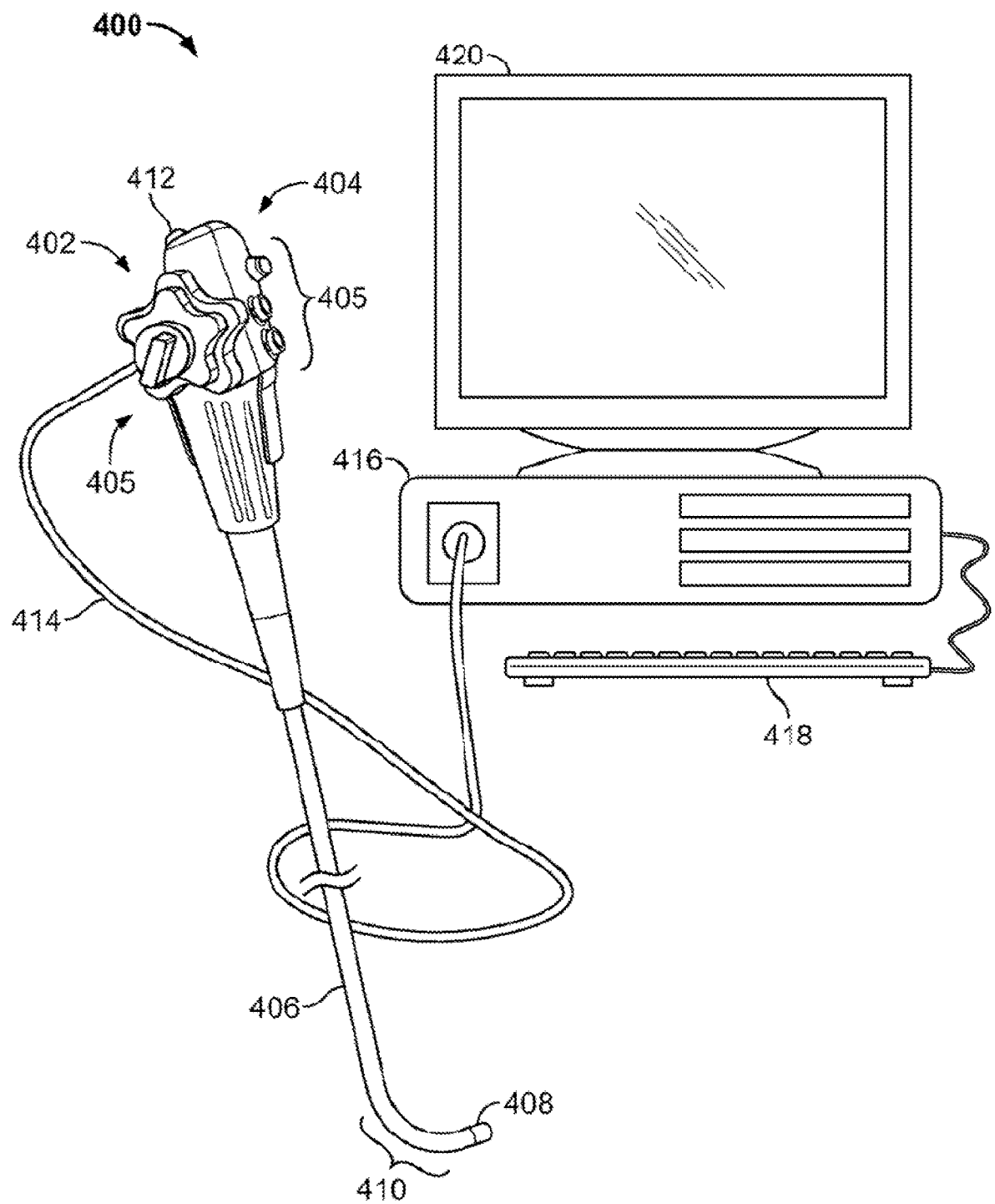
FIG. 1 shows a multiple viewing elements endoscopy system, in accordance with some embodiments.

Reference is now made to FIG. 1, which shows a multiple viewing elements endoscopy system 400, in accordance with some embodiments. System 400 may include a multiple viewing elements endoscope 402, having a multiple viewing elements tip section 408. Multiple viewing elements endoscope 402 may include a handle 404, from which an elongated shaft 406 emerges. Elongated shaft 406 terminates with a tip section 408, which can be turned by way of a bending section 410. Handle 404 may be used to maneuver elongated shaft 406 within a body cavity. The handle 404 may include one or more knobs and/or switches 405 that control bending section 410 as well as functions such as fluid injection and suction. Handle 404 may further include a working channel opening 412 through which surgical tools may be inserted, as well as one or more side service channel openings.

A utility cable 414 may connect between handle 404 and a main control unit 416. Utility cable 414 may include therein one or more fluid channels and one or more electrical channels. The electrical channel(s) may include at least one data cable to receive video signals from the front and side-pointing viewing elements, as well as at least one power cable to provide electrical power to the viewing elements and to the discrete illuminators. Main control unit 416 governs a plurality of operational functionalities of the endoscope. For example, main control unit 416 may govern power transmission to the endoscope's 402 tip section 408, such as for the tip section's viewing elements and illuminators. Main control unit 416 may further control one or more fluid, liquid and/or suction pump, which supply corresponding functionalities to endoscope 402. One or more input devices, such as a keyboard 418, may be connected to main control unit 416 for the purpose of human interaction with main control unit 416. In another configuration (not shown), an input device, such as a keyboard, may be integrated with main control unit 416 in a same casing.

A display 420 may be connected to main control unit 416, and configured to display images and/or video streams received from the viewing elements of multiple viewing elements endoscope 402. Display 420 may further be operative to display a user interface to allow a human operator to set various features of system 400.

Optionally, the video streams received from the different viewing elements of multiple viewing elements endoscope 402 may be displayed separately on display 420, either side-by-side or interchangeably (namely, the operator may switch between views from the different viewing elements manually). Alternatively, these video streams may be processed by main control unit 416 to combine them into a single, panoramic video frame, based on an overlap between fields of view of the viewing elements.

In another configuration (not shown), two or more displays may be connected to main control unit 416, each to display a video stream from a different viewing element of the multiple viewing elements endoscope.

Figure 2:
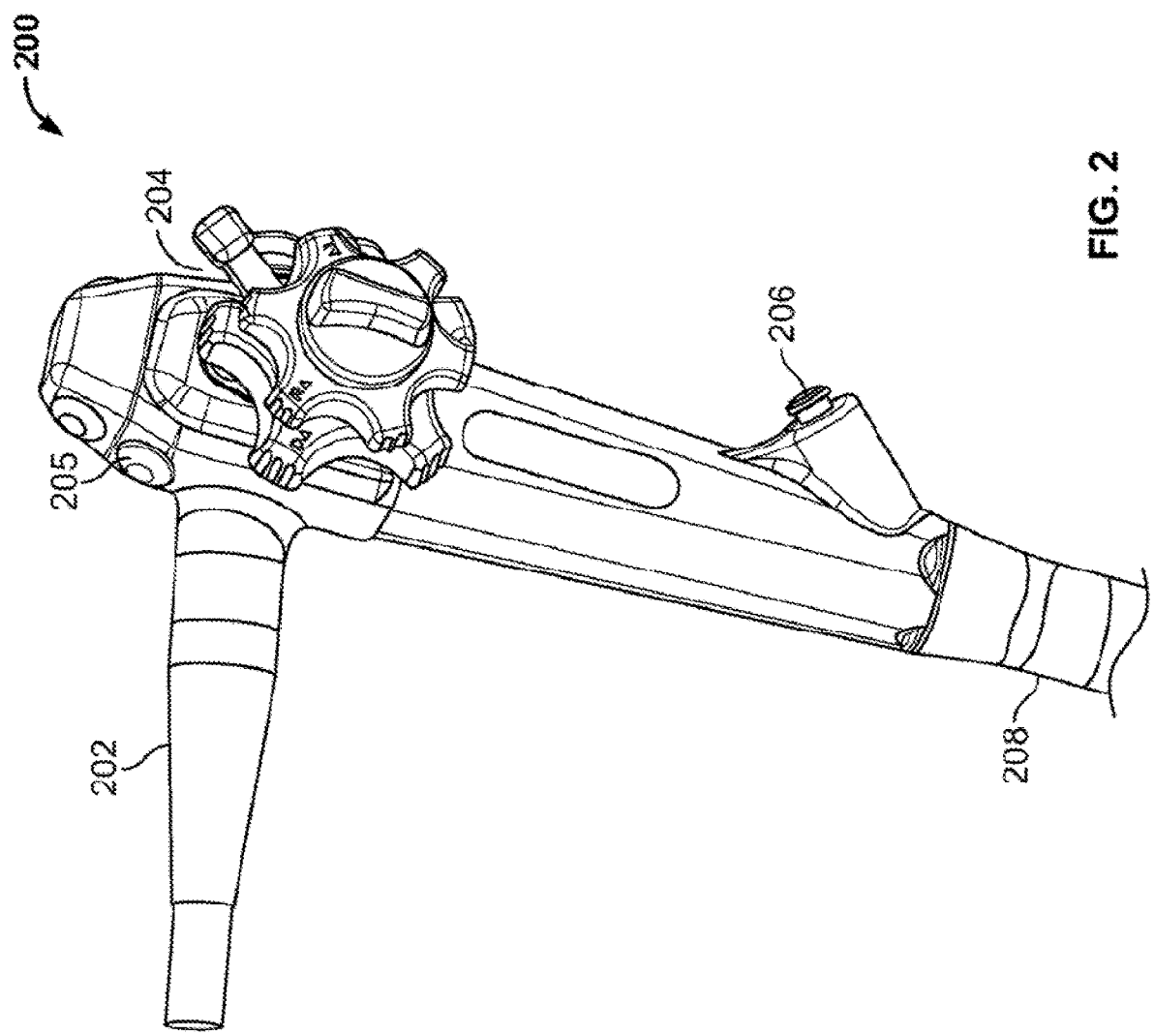
FIG. 2 shows a view of a scope handle of an endoscope, in accordance with some embodiments.

Referring now to FIG. 2, a view of a scope handle 200 of an endoscope, such as endoscope 402 of FIG. 1, is shown. Handle 200 includes various components such as an umbilical tube 202 that connects its control head to a supply plug at the end of a utility cable, such as utility cable 414 of FIG. 1. The control head on handle 200 includes knobs 204 to enable turning of a bending section as well as for functions such as fluid injection and suction. Additionally, handle 200 may include switches/buttons 205. Both knobs 204 and buttons 205 may provide multiple controlling functions. The figure also shows the position of a working channel opening 206 through which surgical tools may be inserted. An insertion portion 208 (shown in part) emerges from handle 200, and has been described as elongated shaft 406 in context of FIG. 1. For purposes of describing the specification, elongated shaft will be known as the 'insertion portion', since it is the part of the endoscope assembly that is inserted inside a body cavity. In embodiments, at a proximal end, handle 200 connected to insertion portion 208 maneuvers it within the body cavity.

Figure 3A:
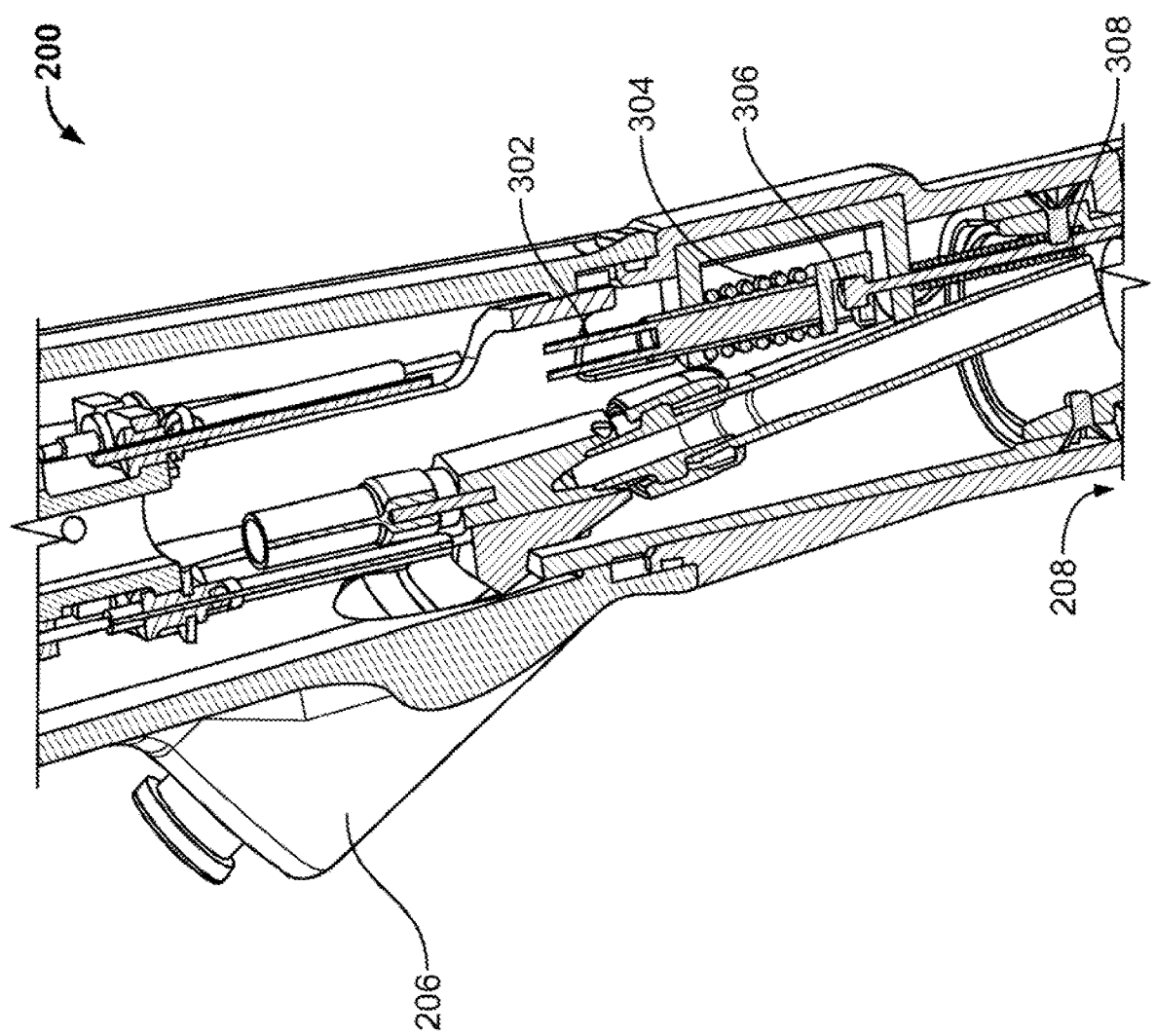
FIG. 3a illustrates a cross-sectional view of a portion of the handle extending from near working channel-opening towards beginning of the insertion portion, in accordance with some embodiments.

FIG. 3a illustrates a cross-sectional view of a portion of handle 200 extending from near working channel opening 206 towards the beginning of insertion portion 208. In embodiments, handle 200 includes an actuator 302 that is responsible for activating a spring 304, thus allowing the spring 304 to modulate its degree of elasticity to change its stiffness. In the embodiments of the present specification, activating is defined as being at least one of modifying the pitch, length, degree of compression, or degree of expansion of the spring. In various embodiments, the spring is any one of a tension/extension spring, compression spring, constant spring, variable spring, coil spring, flat spring, machined spring, In embodiments, actuator 302 and spring 304 are manufactured with Nitinol. Nitinol is an alloy of Nickel and Titanium, and is known for its properties of shape memory and super elasticity. Nitinol deforms at low temperatures and recovers its original shape when heated. In embodiments, this property is used to control or vary the stiffness of insertion portion 208.

In embodiments, a first end of a wire 306 is connected to a shaft over which spring 304 is wound, inside a housing. In the embodiments of the present specification, a wire comprises any single, cylindrical, flexible strand or rod of metal or any member capable of having its extent or degree of mechanical load bearing be modulated. Movement of spring 304 influences stiffness of wire 306. A second end of wire 306 may be connected to a proximal end of a bending section within insertion portion 208. Therefore, movement of spring 304 influences the stiffness of insertion portion 208 along its entire length. In embodiments, a coil 308 is wound around wire 306 to protect it and enable movement of wire 306. In the embodiments of the present specification, movement of the wire causes at least one of the pitch, degree of expansion, degree of compression, and flexibility of the coil to change. In addition, in the embodiments of the present specification, movement of the wire causes at least one of the tensile strength, flexibility, or compressibility of the bending section of the endoscope to change.

Figure 3B:
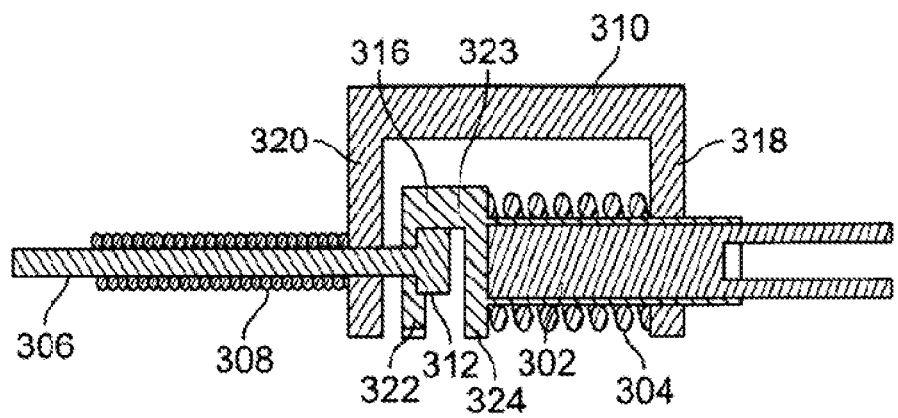
FIG. 3b illustrates another cross-sectional view of a spring and related arrangements in accordance with some embodiments.

Referring now to FIG. 3b, another cross-sectional view of spring 304 and related arrangements is illustrated in accordance with some embodiments. A housing 310 accommodates spring 304 and a dynamic shaft 316. Housing 310 stretches across the length of spring 304, and has two ends—a proximal end 318 and a distal end 320, which may be proximal and distal respectively to a beginning of the handle of the endoscope. Shaft 316 is connected to a distal end of actuator 302 inside housing 310. The proximal end of actuator 302 may continuously exit housing 310 towards a source of energy that actuates spring's 304 movements. Spring 304 is wound around a tubular length of actuator 302, positioned inside housing 310. A proximal end of spring 304 is fixed to the internal surface of proximal end 318 of housing 310. A distal end of spring 304 is fixed to shaft 316.

In one embodiment, shaft 316 is a U-shaped structure, where the two straight parallel edges of its U-shape may be referred to as a first wall 324 and a second wall 322, positioned parallel to one another, each having internal and external surfaces. First and second walls 324, 322, may be connected to each other with a flat base 323 completing the U-shaped form. Wall 324, which is on the proximal side, connects to spring 304 on its external surface, while wall 322 on the distal side, is pierced by, or generally attached to, wire 306. Wire 306 enters shaft 316 from the external surface of wall 322 and is held in place by a stopper 312 on the other side of wall 322. Thus, stopper 312 aids in anchoring of wire 306 inside housing 310. The distal end of wire 306 continuously exits distal end 320 of housing 310, opposite to the side where actuator 302 exits housing 310. Outside housing 310, wire 306 is protected by coil 308 that is fixed to the internal surface of the insertion portion.

Figure 4A:
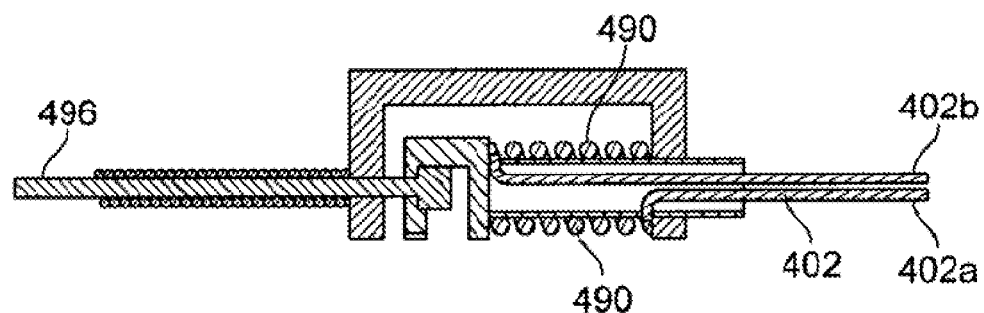
FIG. 4a illustrates an exemplary embodiment of an energy source for an actuator.

Referring now to FIGS. 4a, 4b, 4c, and 4d, exemplary embodiments of energy sources for an actuator, such as actuator 302, are illustrated. FIG. 4a illustrates an actuator 402 that may be energized by an electric current. In embodiments, actuator 402 may comprise two parallel terminals 402a and 402b that are connected to each end of spring 404. In an embodiment, terminal 402a is connected to proximal end of spring 404, and terminal 402b is connected to distal end of spring 404. Any one of the two terminals may be connected to an anode, while the other is connected to a cathode. Electric current may pass through the two terminals, resulting in activation of spring 404, thus allowing spring 404 to modulate its degree of elasticity to change its stiffness. In embodiments, actuator 402 and spring 404 are manufactured with Nitinol. Nitinol is an alloy of Nickel and Titanium, and is known for its properties of shape memory and superelasticity, namely an elastic, reversible response to applied stress. Nitinol deforms at low temperatures and recovers its original shape when heated or placed at low temperatures. Electric current passing through the two terminals heat actuator 402 and as a result spring 404 is also heated, thereby contracting spring 404, resulting in increased stiffness of a wire 414. The second end of wire 414, connected to the proximal end of the bending section within the insertion portion, therefore increases the stiffness of the insertion portion along its entire length. In embodiments, property of superelasticity is used to control or vary the stiffness of the insertion portion.

Figure 4B:
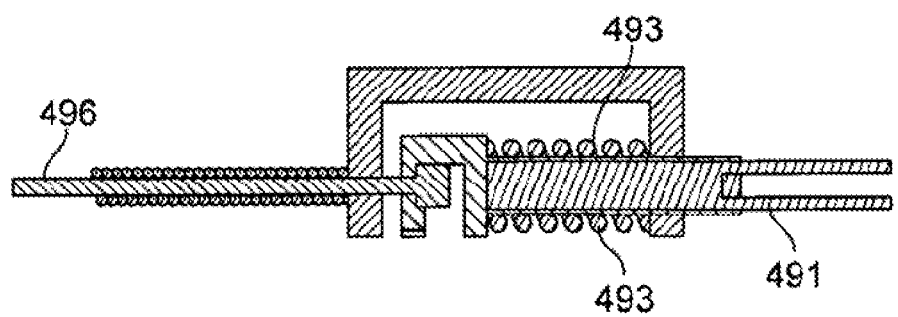
FIG. 4b illustrates another exemplary embodiment of an energy source for an actuator.

FIG. 4b illustrates an actuator 406 that may be energized by a heating body or heat source, such as but not limited to resistance based heater. Actuator 406 is heated, due to thermal conductivity and/or heat transfer from the heating body or heat source. Thus, actuator 406 may be a heat body connected to a spring 408 along the length of the shaft over which spring 408 is wound. In embodiments, heating the actuator 406 activates spring 408, which may be manufactured from a super-elastic material such as Nitinol. Temperature changes applied on the two terminals of heat actuator 406 also causes spring 408 to be heated, thereby causing spring 408 to be in a first configuration, or its original shape, which results in an increase in the stiffness of the insertion portion via pulling or stretching of wire 414. In embodiments, the superelastic property is used to control or vary the stiffness of the insertion portion.

In another embodiment, reduction of temperature of actuator 406 and therefore that of spring 408 results in deformation of both (due to Nitinol deforming at low temperatures), owing to their superelastic property. As a result, lowering the temperature of actuator 406 in order to cool it results in spring 408 to be brought to a second configuration, which causes contraction of wire 414 and subsequently, an increase in the stiffness of the insertion portion. In embodiments, a coolant is used to cool actuator 406 and spring 408.

The extent of stiffness of the insertion tube is therefore controlled by changing temperature of the structure, and therefore of the properties of the wire 414, such that the wire is either pushed or contracted or pulled or expanded.

Figure 4C:
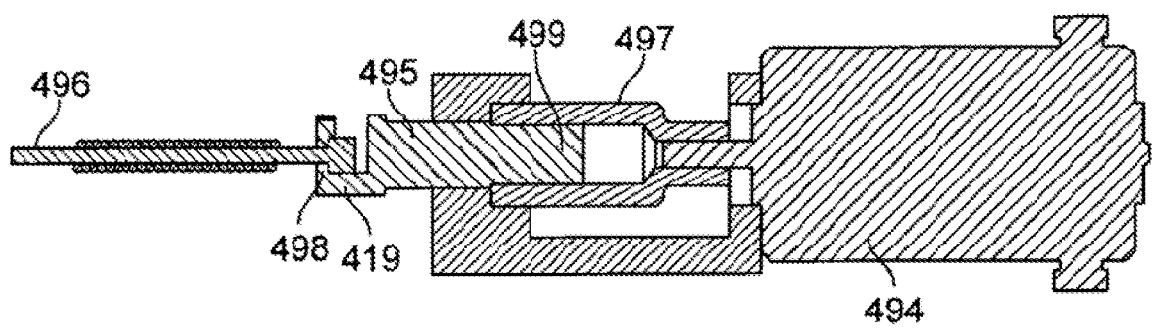
FIG. 4c illustrates yet another exemplary embodiment of an energy source for an actuator.
Figure 4D:
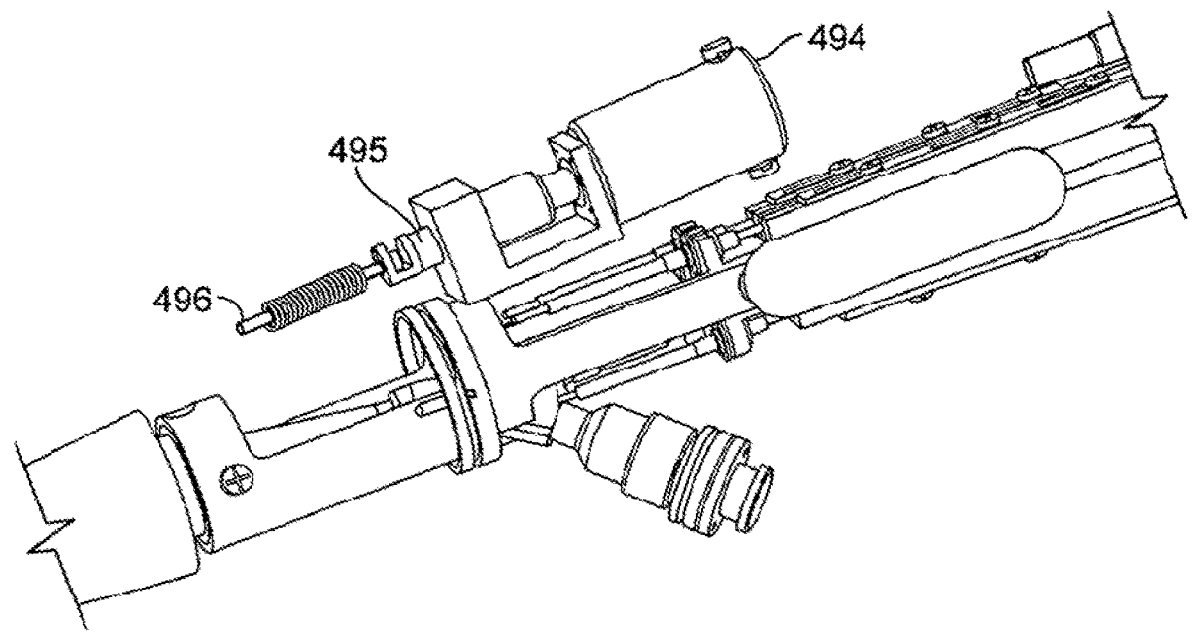
FIG. 4d illustrates still another exemplary embodiment of an energy source for an actuator.

In yet another embodiment, FIG. 4c and 4d illustrate a gear motor 410 that drives a dynamic shaft 412 connected to a wire 414 placed inside the endoscope's insertion portion. In one embodiment, shaft 412 is a U-shaped structure, where the two straight parallel edges of its U-shape may be referred to as a first wall 418 and a second wall 420, positioned parallel to one another, each having internal and external surfaces. First and second walls 418, 420, may be connected to each other with a flat base 419, thus completing the U-shape. Wire 414 stretches over the complete length of the insertion portion and is connected to shaft 412 at proximal end of wire 414. First wall 418 of shaft 412 is connected to wire 414 while a proximal end of second wall 420 is connected to an actuator 416 driven by gear motor 410. In embodiments, operation of gear motor 410 results in stiffening or relaxing of wire 414 with backward or forward movements of shaft 412, respectively, that is pulled by gear motor 410.

Figure 5A:
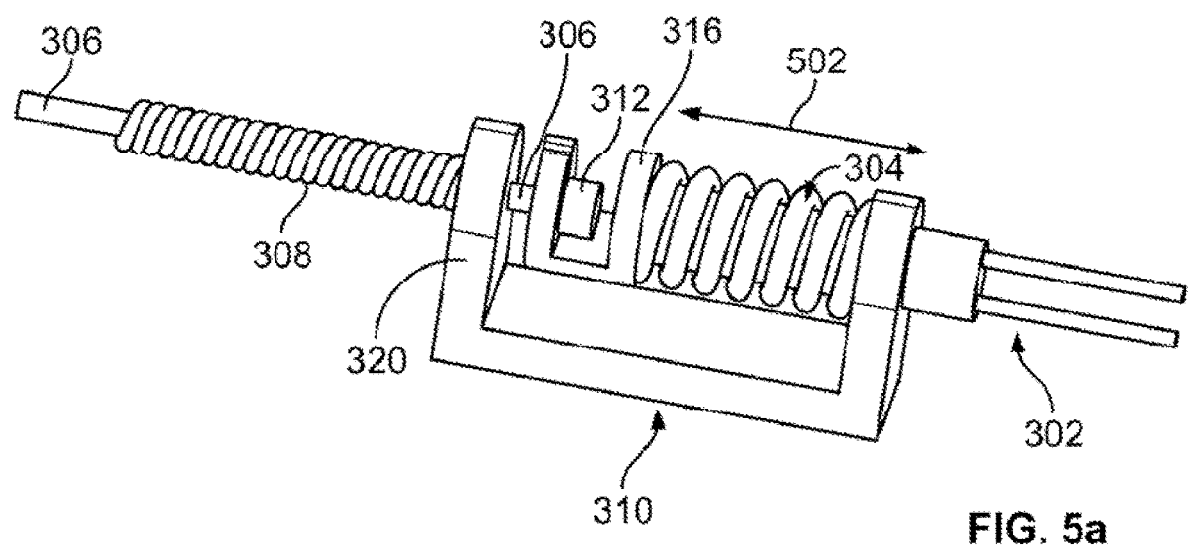
FIG. 5a illustrates another cross-sectional view of the spring and related arrangements described in context of FIGS. 3 and 4, in accordance with some embodiments.

Referring now to FIG. 5a, another cross-sectional view of spring 304 and related arrangements described in context of FIGS. 3 and 4a-4d is illustrated in accordance with some embodiments. Embodiments of FIG. 4a and 4b include wire, coil, and housing configurations (not labelled) similar to those described in context of FIG. 3a and 3b. Hereinafter, wire 306 coil 308, housing 310, and distal end 320 of housing 310, also refer to similar configurations described for FIG. 4a and 4b. In embodiments, coil 308 is wound around wire 306 to protect it and enable movement of wire 306. An arrow 502 illustrates an exemplary direction of movement of spring 304. Movement in one direction may stretch spring 304, such that spring 304 lengthens. As a result, wire 306 also relaxes and decreases the stiffness of the insertion portion, which may make the insertion portion more flexible. Movement in an opposite direction may tighten spring 304, resulting in a tightening of wire 306 and an increase in the stiffness of the insertion portion. Actuator 302, also described above with respect to FIGS. 4a-4d, causes movement of spring 304. An energized actuator 302 may activate spring 304, which results in the tightening of spring 304. Alternatively, when the energy is not provided to actuator 302, or its source is interrupted, spring 304 may return to a loosened or stretched state. While actuator 302 may energize and activate a Nitinol spring causing it to stiffen, in certain embodiments utilizing a mechanical means to move actuator 302 may similarly stiffen or deform spring 304 by a mechanical movement. In embodiments, wire 306 is placed inside coil 308, which is positioned outside of housing 310. Coil 308 is fixed to an internal surface of the insertion portion along its length, and is also fixed to an external surface of distal end 320 of housing 310. As a result, when spring 304 is stiffened, wire 306 is pulled, resulting from the pulling motion by actuator 302.

Figure 5B:
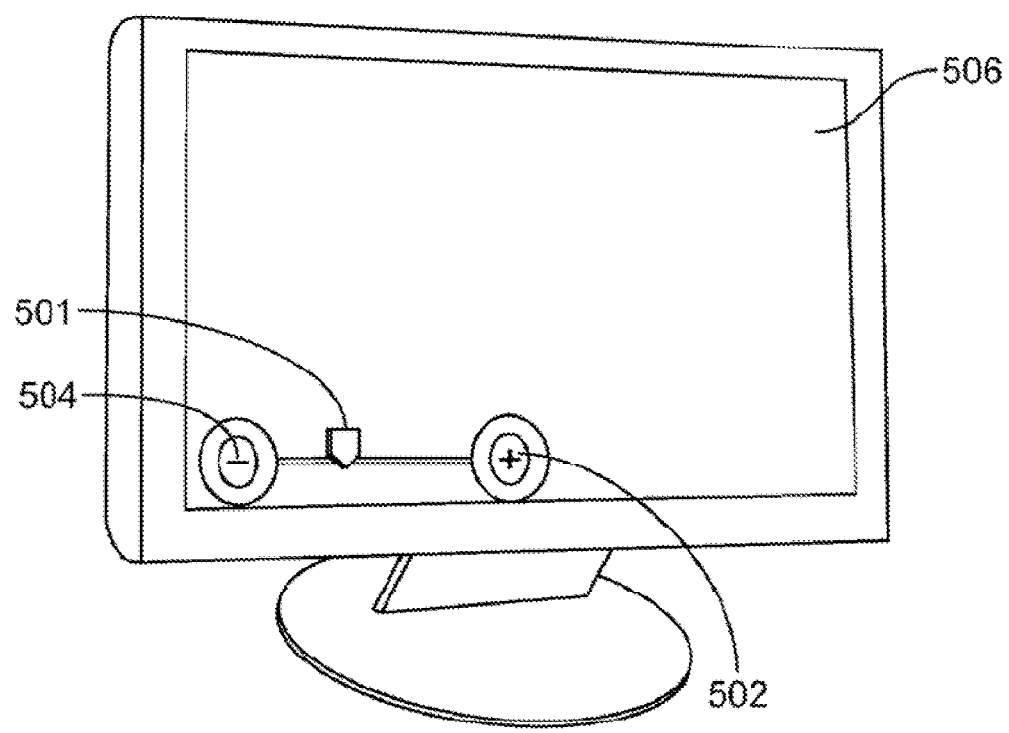
FIG. 5b shows an exemplary display illustrating a degree of stiffness of an insertion tube, in accordance with some embodiments.

In operation, as actuator 302 is energized, spring 304 is activated. Activation of spring 304 results in a change in its shape owing to superelastic properties of Nitinol. Consequently, dynamic shaft 316 moves while pulling or pushing wire 306, as wire 306 is also connected to shaft 316. The stiffness character of the insertion portion is influenced by pulling or pushing the wire, influenced respectively by heating or cooling actuator 302. In embodiments, controlling the amount of energy provided to actuator 302 may further control the degree of stiffness of the insertion portion. In embodiments, a controller to control the degree of energy provided to actuator 302 and therefore the degree of stiffness of the insertion portion is provided in either the handle of the endoscope, the main control unit connected to the endoscope, through a foot pedal attached to the endoscope, or through any other means. The control mechanism may be provided through an interface such as a push button, a valve, a nob, or any other digital or analogue interface. As the energy provided to actuator 302 is increased, wire 306 is pulled more, and the degree of stiffness increases. In embodiments, one or more screens connected to the system may display the use of a control to control the stiffness, and may even display a degree of stiffness achieved through the control. For example a display may illustrate the stiffness in effect through a binary illustration, such as whether the insertion tube is or is not stiff. In another example, a display may indicate a degree of stiffness over a numerical or any other scale, such as 1 to 4, where 1 may be first degree of stiffness and 4 may be the highest degree of stiffness that can be applied to the insertion tube, or vice versa. In yet another example, also illustrated in FIG. 5b, a degree of stiffness may be indicated through a display 506 by means of a slider 501 between standard "+" and "−" symbols 503 and 504, respectively indicating maximum and minimum degrees of stiffness.

Figure 6:
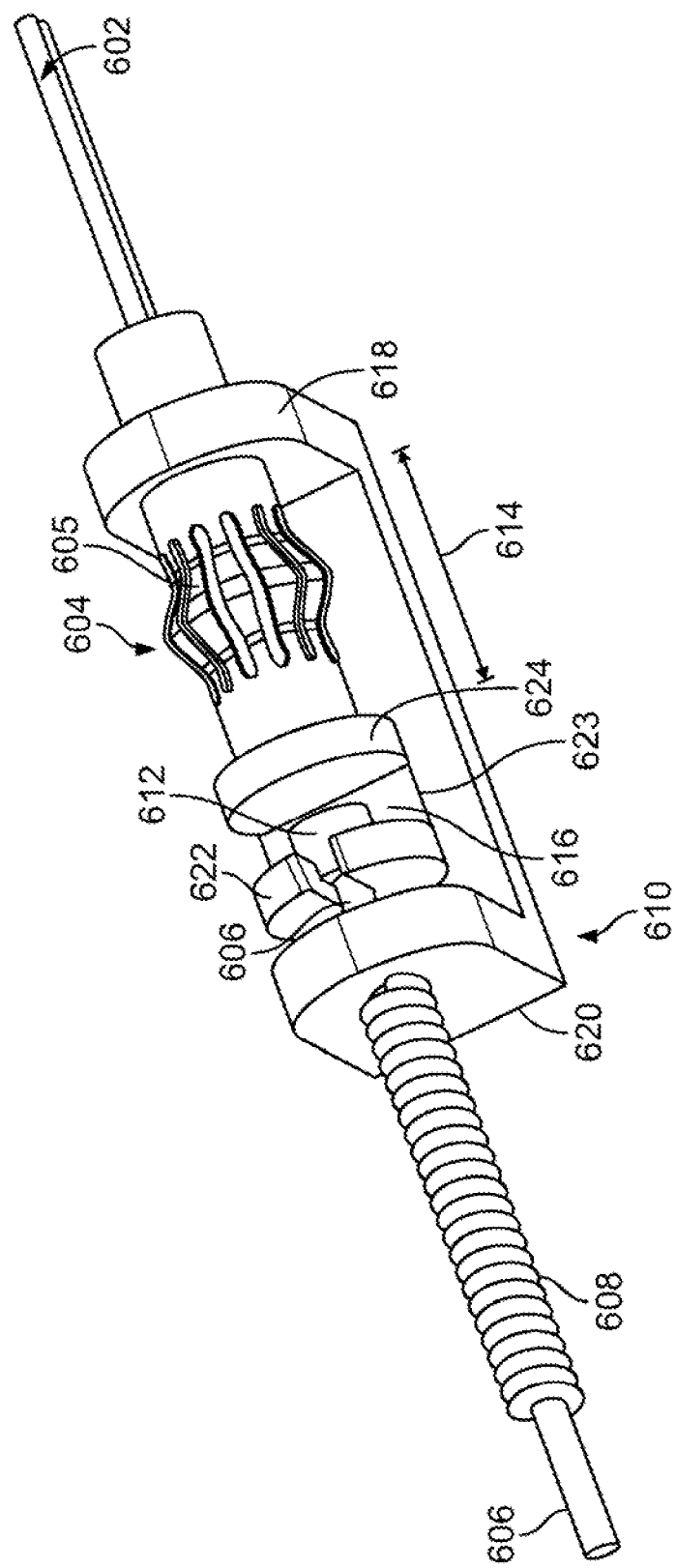
FIG. 6 illustrates an alternative embodiment of an arrangement to influence variable stiffness of an insertion portion in an endoscope.

FIG. 6 illustrates an alternative embodiment of an arrangement to manipulate and vary the stiffness of an insertion portion in an endoscope. In this embodiment, the spring is replaced by a tube 604, which is also manufactured with Nitinol. Tube 604 comprises slits 605 along its tubular walls, and along its longitudinal axis. The slits 605 may stretch across a portion of tube 604 and may be centered at the center of the total length of tube 604. In embodiments, the slits 605 are typically equidistant from each other, spaced throughout the circumference of tube 604. Similar to the previous embodiment, tube 604 may be placed over an actuator 602, inside a housing 610. Housing 610 accommodates tube 604 and a dynamic shaft 616. Housing 610 may stretch across the length of tube 604, and have two ends—a proximal end 618 and a distal end 620, which may be proximal and distal respectively to a beginning of the handle of the endoscope. Shaft 616 may be connected to a distal end of actuator 602 inside housing 610. The proximal end of actuator 602 may continuously exit housing 610 towards a source of energy that actuates tube's 604 movements. Tube 604 may be placed around a tubular length of actuator 602, positioned inside housing 610. Proximal end of tube 604 is fixed to internal surface of proximal end 618 of housing 610. Distal end of tube 604 is fixed to shaft 616.

In one embodiment, shaft 616 is a U-shaped structure, where the two straight parallel edges of its U-shape may be referred to as a first wall 624 and a second wall 622, positioned parallel to one another, each having internal and external surfaces. First and second walls 624, 622, may be connected to each other with a flat base 623, thus completing the U-shape. External surface of wall 624, which is on the proximal side of the endoscope handle, connects to tube 604, while wall 622 on the distal side, is pierced by wire 606. Wire 606 enters shaft 616 from the external surface of wall 622 and is held in place by a stopper 612 on the other side of wall 622. Thus, stopper 612 aids in anchoring of wire 606 within the inside of housing 610. The distal end of wire 606 continuously exits distal end 620 of housing 610, opposite to the side where actuator 602 exits housing 610. Outside housing 610, a coil 608 that is fixed to the internal surface of insertion portion 208 protects wire 606. An arrow 614 illustrates exemplary direction of movement of tube 604, which is caused by energising or de-energising of actuator 602. Actuator 602 may be one of several embodiments described previously, such as in context of FIGS. 4a, 4b, 4c, and 4d. Additionally, operation of tube 604 mechanism may be similar to operation of spring 304 mechanism, similar to that described in context of FIG. 5a.

Figure 7A:
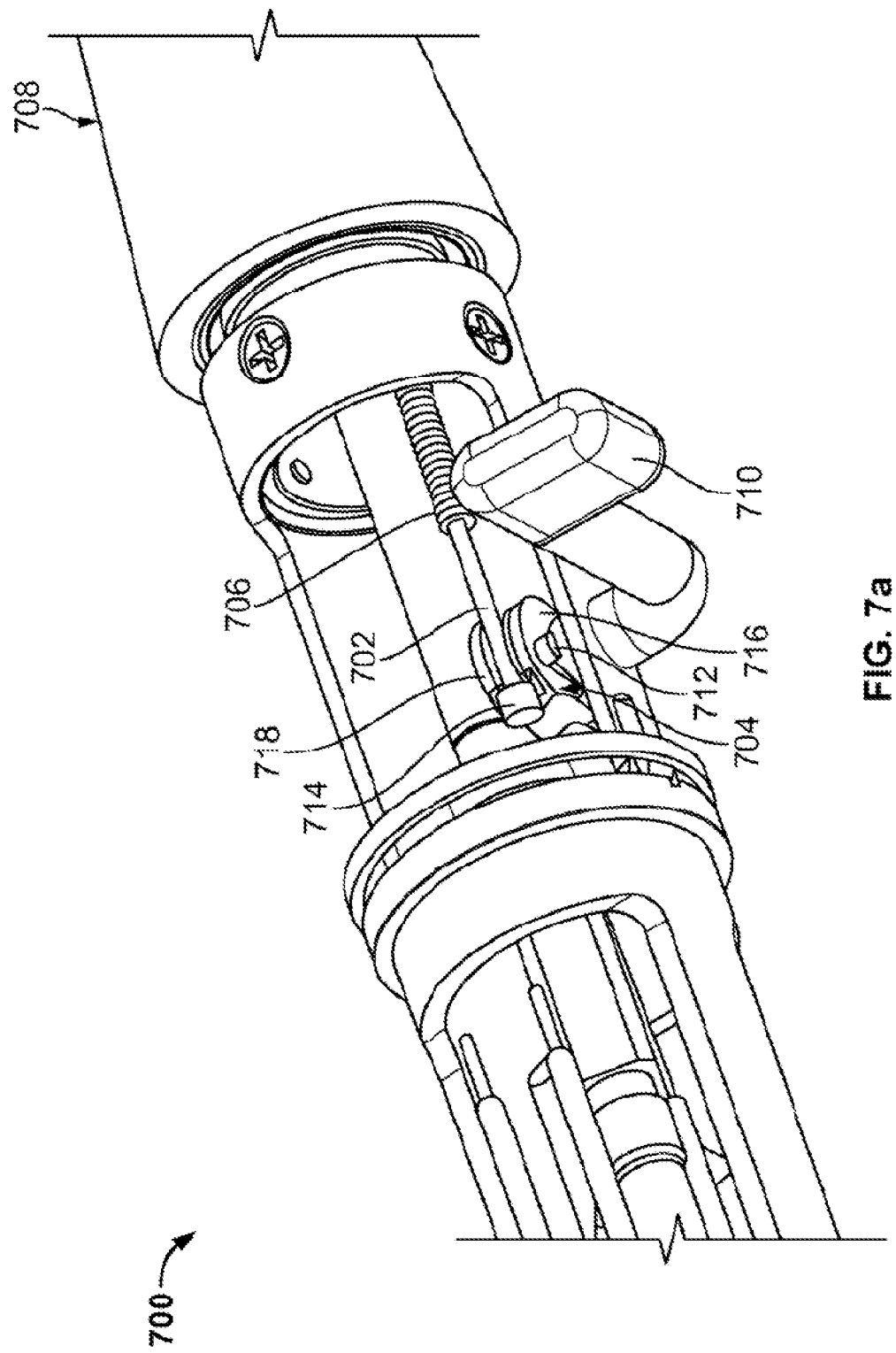
FIG. 7a illustrates a portion of an endoscope handle with an elliptical wheel arrangement that enables variable stiffness of an insertion portion of an endoscope, in accordance with some embodiments.

FIG. 7a illustrates a portion of an endoscope handle with an elliptical wheel mechanism 700 that enables variable stiffness of an insertion portion 708 of the endoscope. In an embodiment, an elliptical wheel 704 comprises two side portions—a first side portion 716 and a second side portion 718 that sandwich a center portion. The edges of first portion 716 and second portion 718 rest slightly above the center portion of the sandwich. Thus, the diameter of first portion 716 and second portion 718 is larger than the diameter of the center portion. In embodiments, a wire 702 rests on an outer edge of the center portion, between two sides 716 and 718 of wheel 704. In embodiments, wire 702 is connected at its proximal end to a stopper 714. Stopper 714 rests against edges two sides 716 and 718 of wheel 704. Wheel 704 may have a shape similar to that of an ellipse. In embodiments, one or both of the longer edges of elliptical wheel 704 may have an indentation such that the indentation provides a recess or a notch for stopper 714 to rest and stop rotation of wheel 704. Thus, stopper 714 enables anchoring of wire 702 with wheel 704. At its other end, wire 702 is connected to a proximal end of a bending section within insertion portion 708. In embodiments, wire 702 is placed inside a coil 706. Coil 706 enables movement of wire 702, and is fixed to the internal surface of insertion portion 708.

In embodiments, wheel 704 is connected to a shaft 712, which in turn is connected to a lever 710. Thus, lever 710 operates wheel 704. In embodiments, lever 710 is manually operated, and the extent of its rotation influences the degree of stiffness of insertion portion 708. In operation, rotation of lever 710 rotates wheel 704, which influences wire 702. Consequently, wire 702 either tightens or relaxes, based on the direction of rotation of lever 710.

Figure 7B:
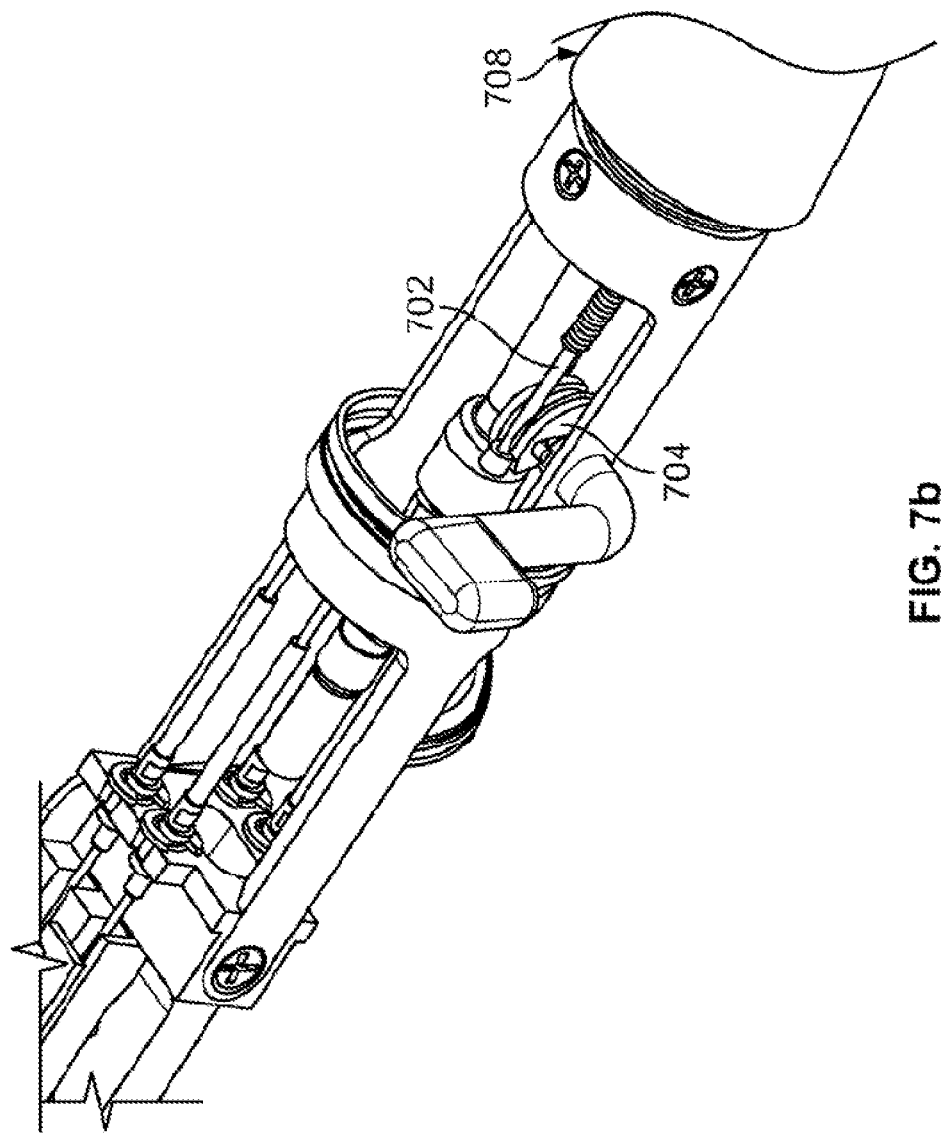
FIG. 7b illustrates a perspective view of the endoscope handle with the elliptical wheel arrangement of FIG. 7a, in accordance with some embodiments.

FIG. 7*b* illustrates another perspective view of the endoscope handle with the elliptical wheel arrangement of FIG. 7*a*. In the arrangement, wheel 704 is located at a proximal end of the endoscope's handle, and wire 702 extends towards a distal end into insertion portion 708.

Figure 7C:
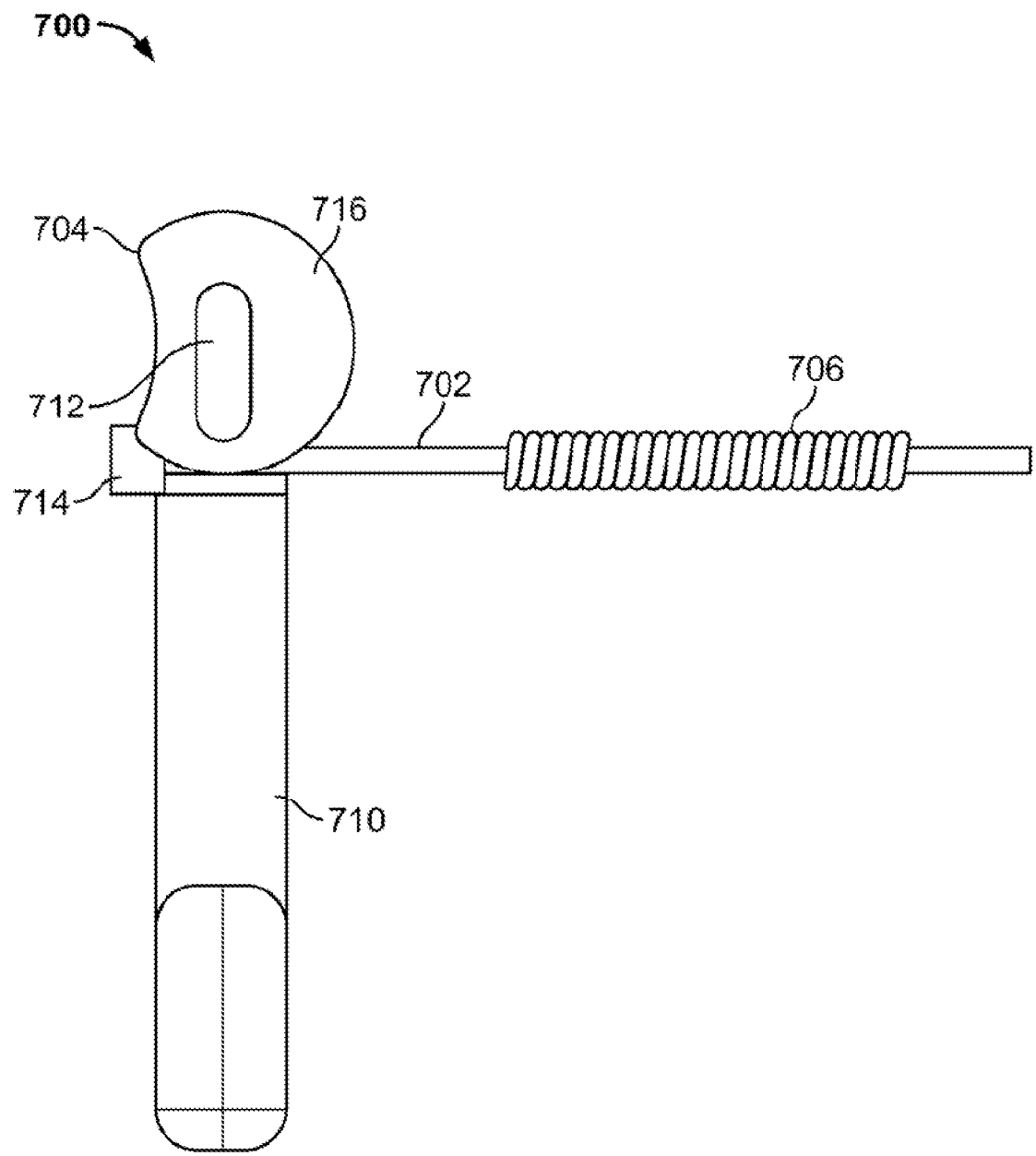
FIG. 7c illustrates an enlarged view of the elliptical wheel arrangement, in accordance with some embodiments.

FIG. 7*c* illustrates an enlarged two-dimensional view of assembly 700, in accordance with some embodiments. In embodiments, wheel 704 has an asymmetric shape, similar to an ellipse. In this figure, one side 716 is visible, and the second side cannot be seen. Central edge of wheel 704 is also hidden behind side 716, between the two sides. Wire 702 is seen connected to stopper 714 and passing over the central edge of wheel 704. The concentric center of elliptical wheel 704 allows its radius to increase as wheel 704 rotates. Increased radius results in tightening of wire 702. Shaft 712, connected to lever 710, rotates with the movement of lever 710. Wheel 704 is placed on shaft 712 and rotates with it. In embodiments, wire stopper 714 is adapted to fix position of wire 702 relative to wheel 704. In embodiments, one of the longer edges of elliptical wheel 704 may have an indentation such that the indentation provides a recess or a notch for stopper 714 to rest and stop rotation of wheel 704. Thus, stopper 714 enables anchoring of wire 702 with wheel 704. At its other end, wire 702 is connected to a proximal end of a bending section within insertion portion 708. Once the wheel stops rotating, wire 702 may not move further around outer edge of centre portion of wheel 704, thus fixing location of wire 702 relative to wheel 704.

Figure 8A:
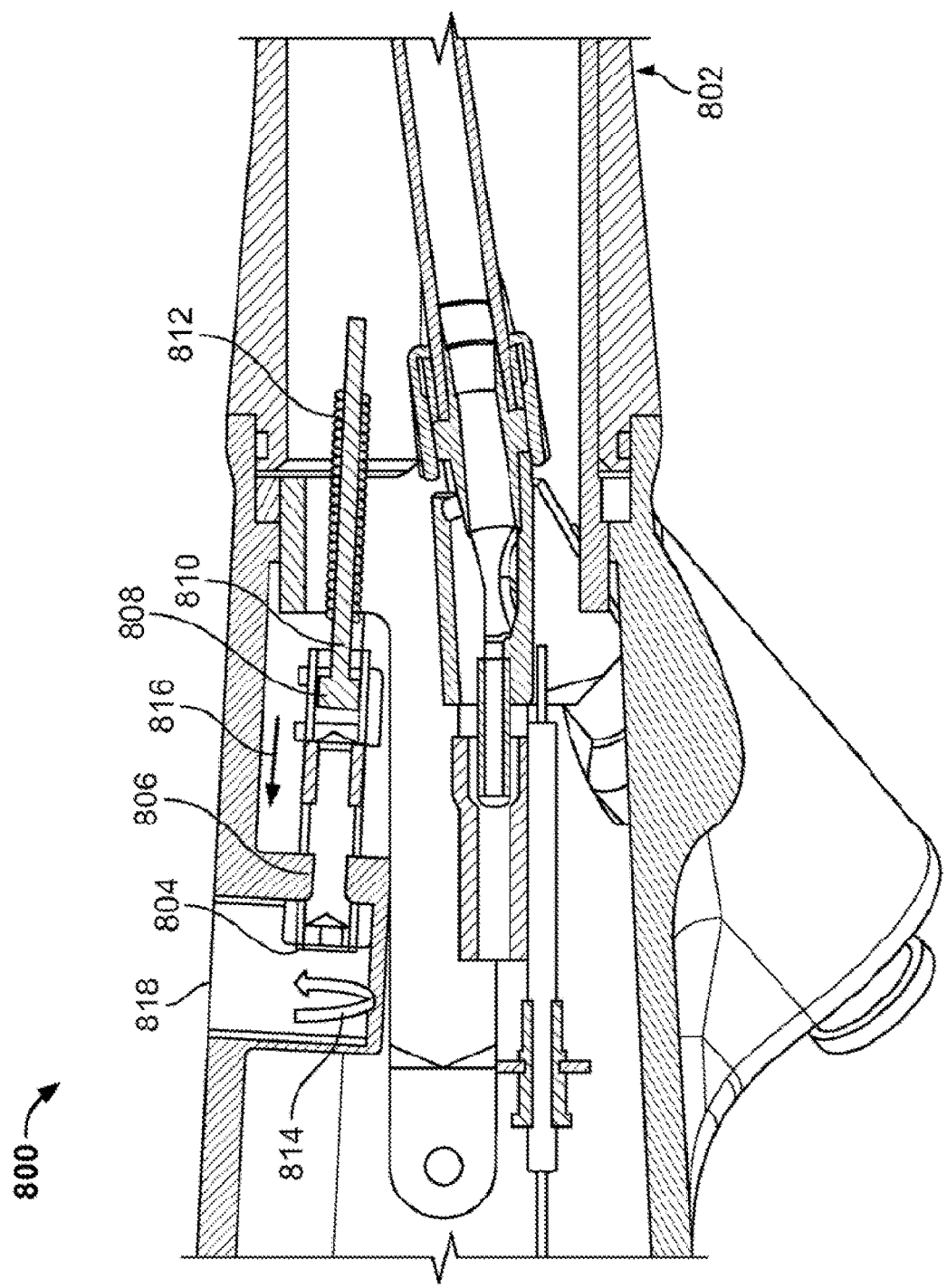
FIG. 8a illustrates a cross-sectional view of yet another embodiment of a screw mechanism within a handle portion of an endoscope, in accordance with some embodiments.
Figure 8B:
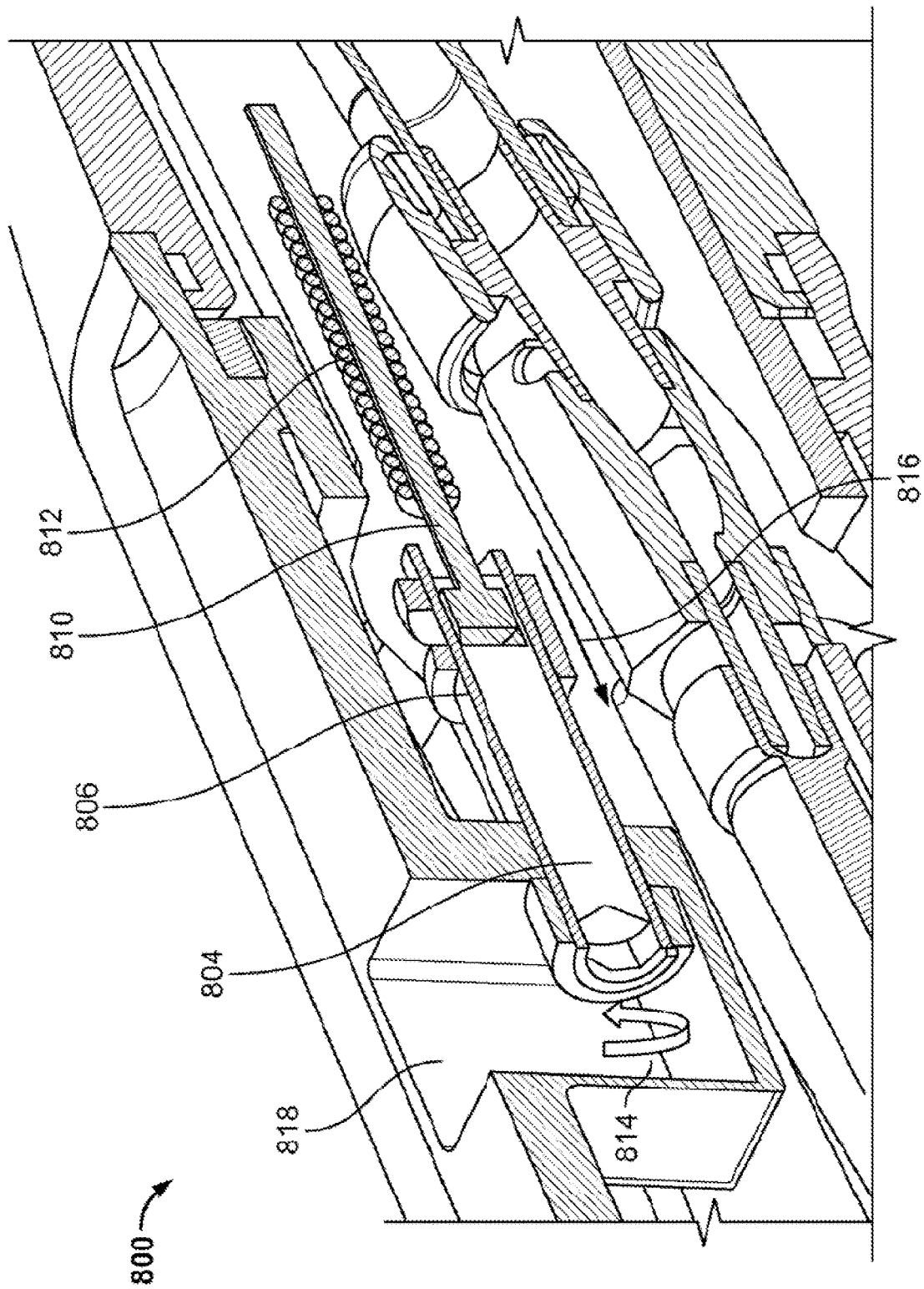
FIG. 8b illustrates a cross-sectional view of yet another embodiment of a screw mechanism within a handle portion of an endoscope, in accordance with some embodiments.

FIG. 8*a* and 8*b* illustrate cross-sectional views 800 of another embodiment for varying the stiffness of an insertion portion 802 of an endoscope involving a screw mechanism located within the handle of an endoscope. Simultaneously referring to FIG. 8*a* and 8*b*, the mechanism includes a screw 804 placed within a housing 806 located in the handle of the endoscope. In embodiments, housing 806 further includes an internal housing (further illustrated in FIG. 9) to house a wire stopper 808. In embodiments, internal housing moves in accordance with a tightening/releasing movement of screw 804, in a direction that is at least one of a distal direction and a proximal direction along the longitudinal axis of the endoscope assembly. In embodiments, a proximal end of a wire 810 is connected to stopper 808. Distal end of wire 810 is connected to a proximal side of a bending portion at distal end of insertion portion 802. In embodiments, an opening 818 in the endoscope handle provides an optimal space and location suitable to place the screw mechanism in accordance with described embodiments. In some embodiments, a knob on the handle, such as knob 405 described with reference to FIG. 1, may be used to rotate the screw 804. The knob is in communication with the screw such that a rotation of the knob causes a rotation of the screw. In some embodiments, the physical connection between the knob and the screw 804 may be geared such that a large rotation of the knob 804 would cause a smaller rotation of the screw or a small rotation of the knob would cause a larger rotation of the screw 804.

Figure 9:
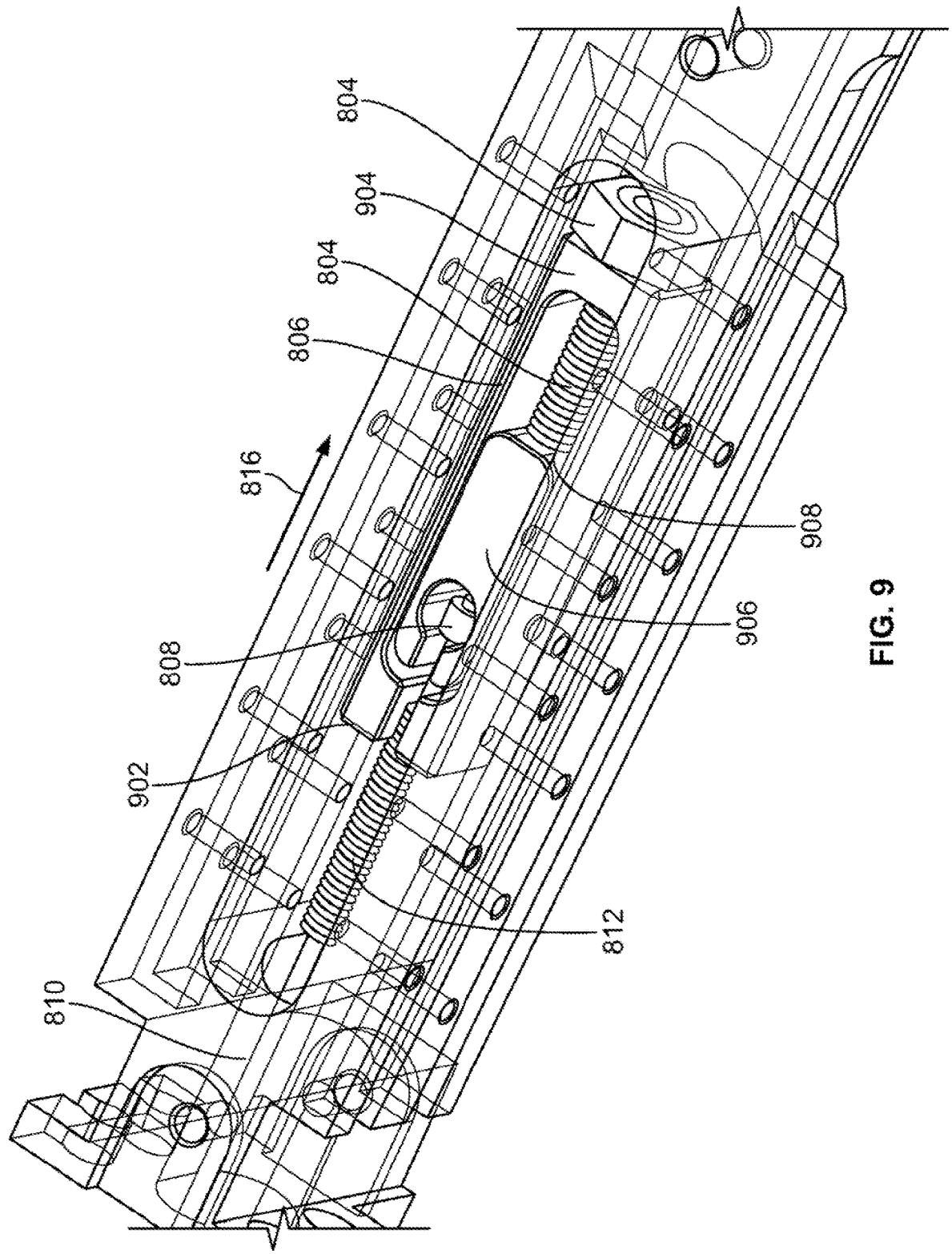
FIG. 9 illustrates a three-dimensional view of the screw mechanism of FIG. 8a and 8b, in accordance with some embodiments.

Referring to FIG. 9 in combination with FIG. 8*a* and 8*b*, a three-dimensional view of the screw mechanism of FIG. 8*a* and 8*b* is illustrated. In addition to components described in context of FIG. 8*a* and 8*b*, FIG. 9 illustrates an internal housing 906, placed within housing 806. Internal housing 906 moves with tightening/releasing of screw 804. In embodiments, as screw 804 is tightened, internal housing 906 moves in a direction of its proximal end 908, towards a proximal end 904 of housing 806. In operation, screw 804 may be rotated around a longitudinal axis of the endoscope's handle. Rotating screw 804 may cause internal housing 906 to move along the longitudinal axis. In embodiments, rotation of screw in a clock-wise direction 814 may move internal housing 906 in a proximal direction 816, towards a proximal end of the endoscope's handle. In embodiments, distal end of wire 810 is connected to a proximal end of a bending section within the endoscope. In embodiments, wire 810 is placed within a coil 812, which enables movement of wire 810. Coil 812 is fixed to the internal surface of insertion portion 802.

Screw 804 is connected to proximal end 908. In embodiments, screw 804 is screwed inside internal housing 906 through its proximal end 908. Rotation of screw 804 moves internal housing 906 closer to proximal end 904 of housing 806, in proximal direction 816. Consequently, wire 804 is pulled resulting in stiffening of the insertion portion. When screw 804 is released, internal housing 906 moves towards a distal end 902 of housing 806, resulting in a relaxed insertion portion. Therefore, movement of screw 804 influences tightening or loosening of wire 810.

Figure 10:
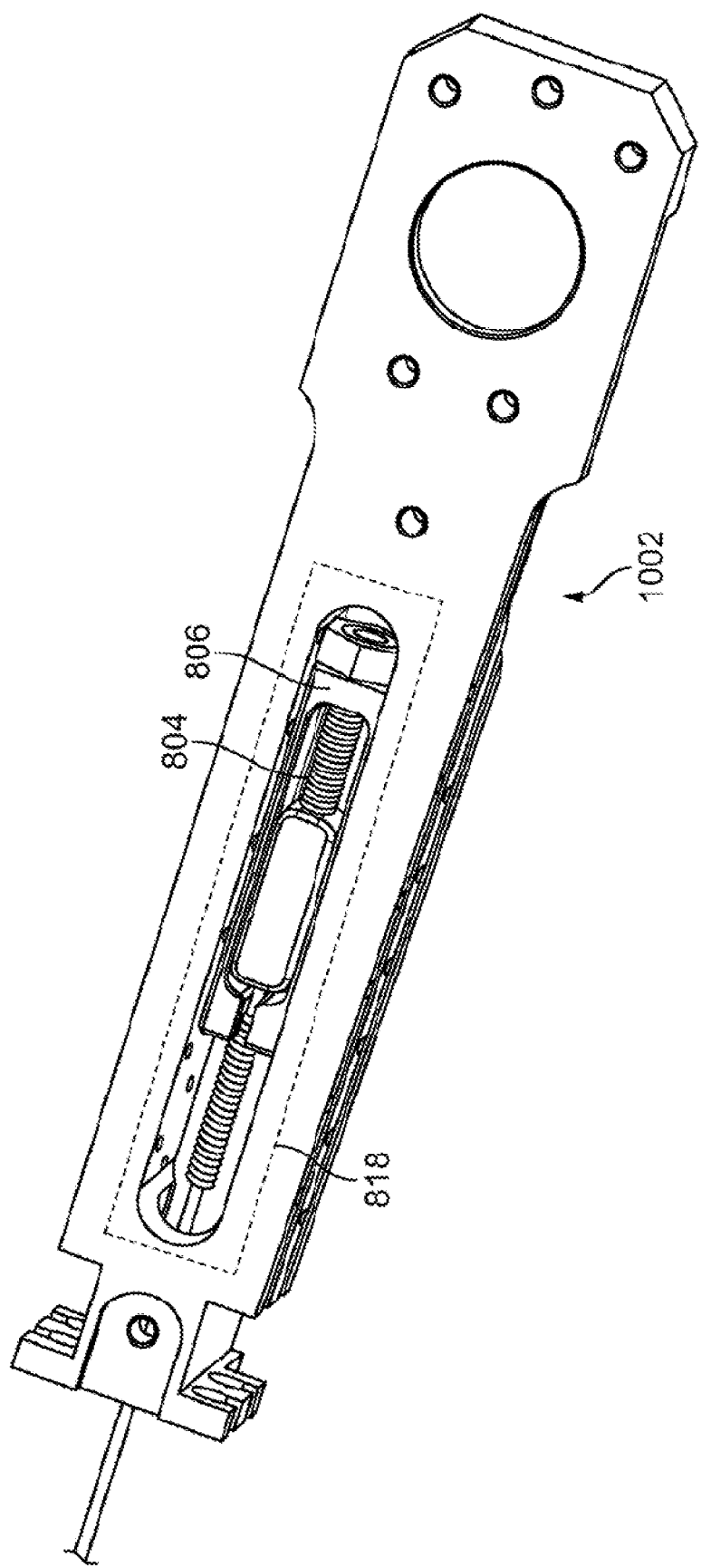
FIG. 10 illustrates a housing and a screw mechanism placed within an opening of a handle of an endoscope, in accordance with some embodiments.

In embodiments, an opening 818 in the endoscope handle provides an optimal space and location suitable to place the screw mechanism in accordance with described embodiments. FIG. 10 illustrates housing 806 and the screw mechanism placed inside opening 818 in a handle 1002 of the endoscope. In embodiments, internal design of scope handle 1002 allows secure placement of the screw mechanism. FIG. 10 illustrates a view of handle 1002 when it is open. Once handle 1002 is closed and locked, the screw mechanism is invisible, secure, and intact. The mechanism may be operated, likely to tighten screw 804, during a maintenance activity when handle 1002 is unlocked and opened to reveal the screw mechanism.

Figure 11A:
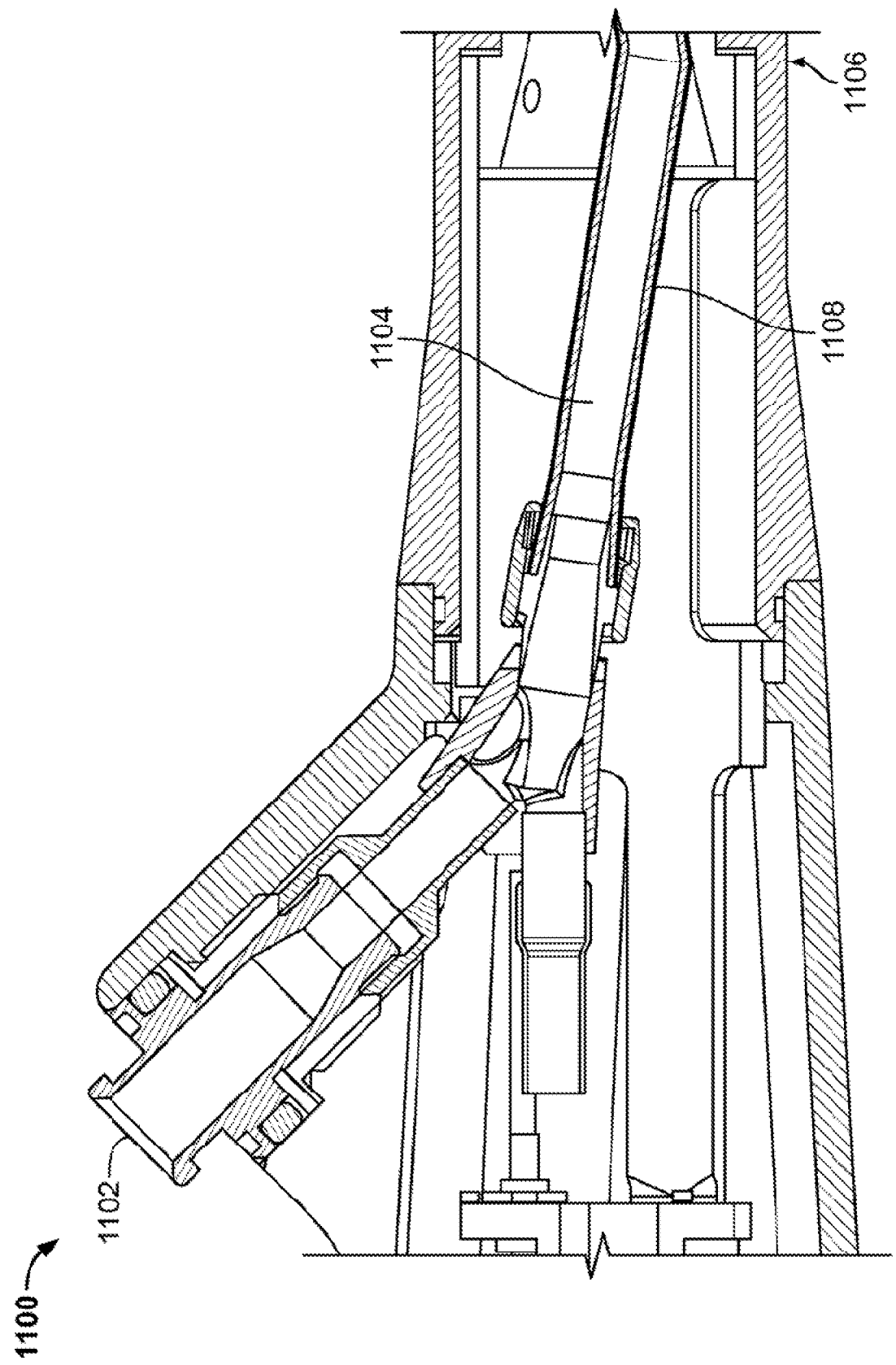
FIG. 11a illustrates another embodiment of a mechanism that reinforces the stiffness of an insertion portion of an endoscope, in accordance with some embodiments.
Figure 11B:
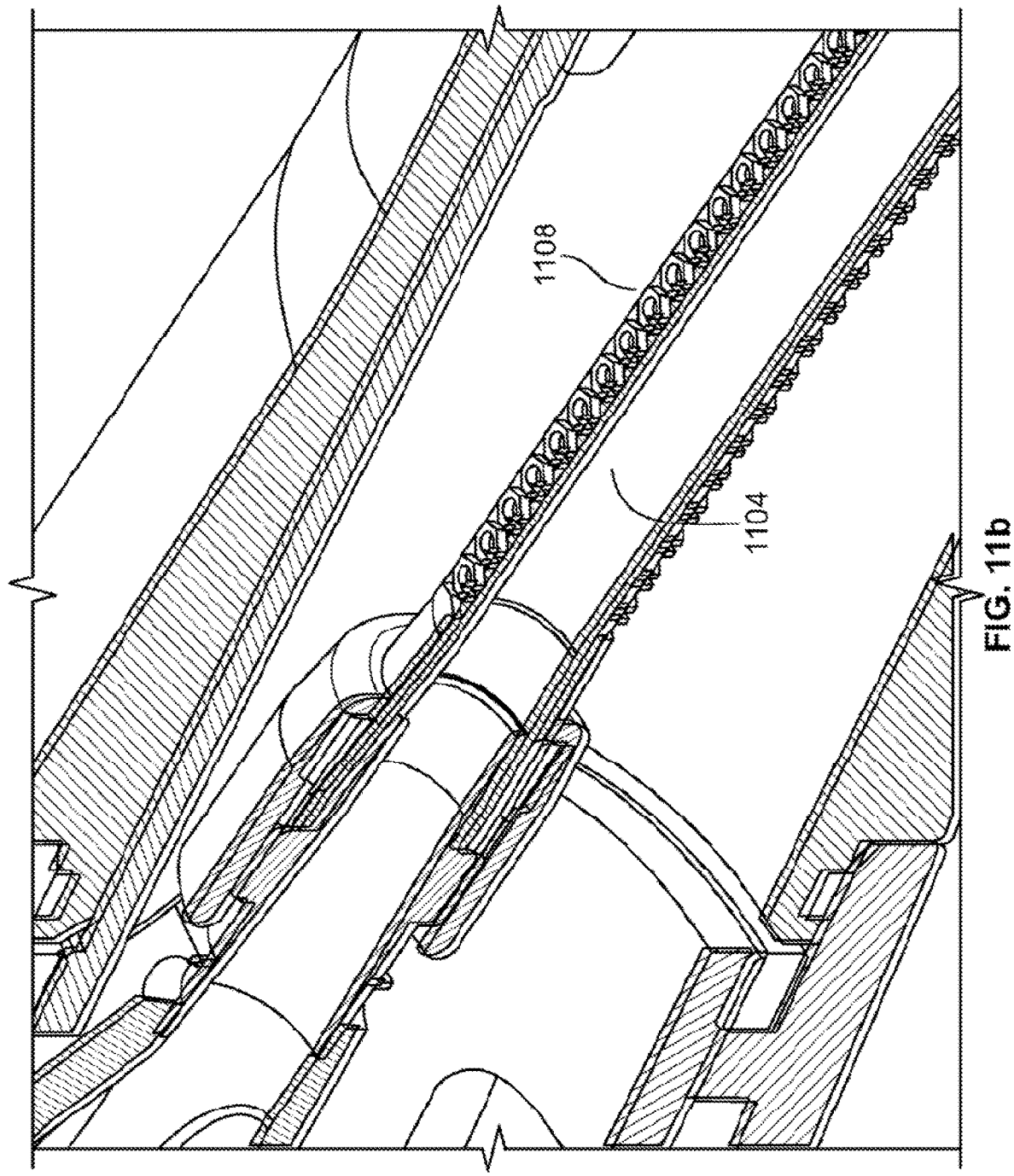
FIG. 11b illustrates another view of the embodiment of FIG. 11a, in accordance with some embodiments.

Referring to FIG. 11*a* and 11*b*, an additional embodiment is described, which influences stiffness of an insertion portion of an endoscope. FIG. 11*a* illustrates a cross-sectional view of a handle 1100. A service channel opening leads to a working channel 1104 inside handle 1100. Working channel 1104 extends towards tip section of the endoscope, stretching over entire length of an insertion portion 1106. In embodiments, an enforcement layer 1108 is placed over an outer periphery of working channel 1104. In embodiments, layer 1108 may be manufactured from a metal that is from the family of stainless steel metals, or any other material that may stiffen working channel 1104 such that utility of working channel 1104 remains unaffected. Physicians are able to insert surgical tools and/or equipment to perform procedures through working channel 1104 that is covered by layer 1108. Working channel 1104 stretches over entire length of insertion portion 1106, therefore layer 1108 may influence stiffness characteristic of insertion portion 1106, for example by providing permanent stiffness to insertion portion 1106.

FIG. 11b illustrates a cross-sectional view of working channel 1104 inside the endoscope handle. The figure also clearly illustrates enforcement layer 1108 on the outer periphery of working channel 1104.

Although the present specification has been described with particular focus on an actuator that can controls a super-elastic element in order to vary stiffness of an insertion portion in an endoscope assembly, the present specification is also designed to vary stiffness through means of fluid and gas provided within the insertion portion. Therefore, various embodiments of the present specification describe elements (solid, liquid, and gas) that are controlled through different mechanisms to vary stiffness of an insertion portion in an endoscope.

Figure 12:
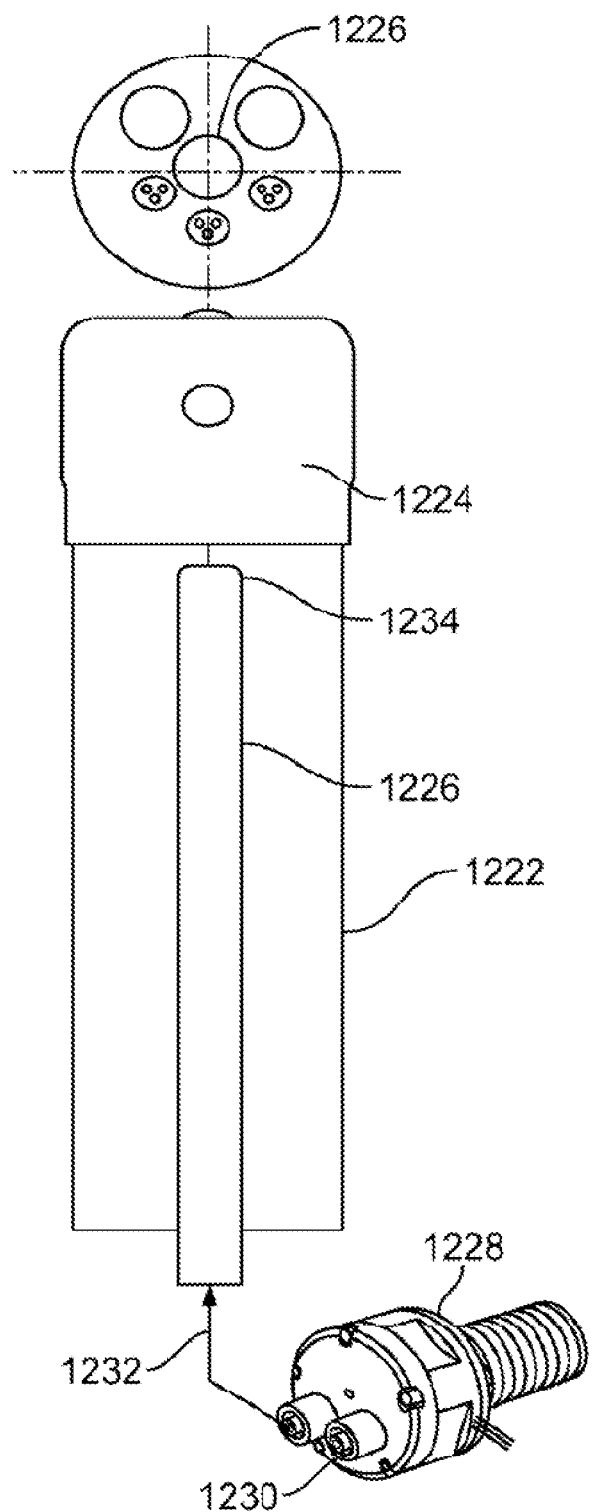
FIG. 12 shows a longitudinal cross-sectional view of a portion of an elongated shaft in an endoscope in accordance with some embodiments.

Referring now to FIG. 12, a longitudinal cross-sectional view of a portion of an elongated shaft in an endoscope is shown, in accordance with some embodiments. For purposes of describing the specification, elongated is termed as the 'insertion portion', since it is the part of the endoscope assembly that is inserted inside a body cavity.

An insertion portion 1222 terminates at a tip section 1224, which is at the distal end (that is, the end that is farthest from the endoscope handle) of insertion portion 1222. In embodiments, at a proximal end, a handle connected to insertion portion 1222 assists/help maneuvers the insertion portion within the body cavity. The arrangement of these components is described above with reference to FIG. 1. In some embodiments, a flexible tube 1226 extends from the proximal end of insertion portion 1222 along its entire length. In embodiments, flexible tube 1226 is a separate tube outside a working channel and inside insertion portion 1222. In embodiments, length of flexible tube 1226 may vary with the length of insertion portion 1222.

Diameter of flexible tube 1226 may also vary to adapt to the endoscope device where is it embedded. In embodiments, flexible tube 1226 may have an amorphous shape that adapts to space available within insertion portion 1222. In embodiments, flexible tube 1226 is manufactured with a polymer that is used for conductivity of fluid under pressure. Examples of such polymer may include, but are not limited to, Polyurethane, Polyamide, Polyethylene, Polypropylene, Nylon, Silicon, and TPE.

The illustrated embodiment shows flexible tube 1226 terminating at tip section 1224. In alternative embodiments, flexible tube 1226 terminates some distance prior to tip section 1224, and within the bending section of insertion portion 1222. In other embodiments, flexible tube 1226 terminates just before a first vertebra of the bending section, or at a proximal end of the bending section. In embodiments, flexible tube 1226 is configured to enclose a fluid, such as but not limited to water. In embodiments where water inflates flexible tube 1226, the water may be sourced from the same supply that feeds the injector channel. Flexible tube 1226 may be sealed at its distal end, referred to as a sealed end 1234, such that it carries a volume of water enclosed within flexible tube 1226. An increase in this volume results directly in an increase of pressure of the water inside the flexible tube 1226, which, in turn, results in an increase in stiffness (or decrease in flexibility) of flexible tube 1226. Conversely, a decrease in this volume results directly in a decrease of pressure of the water inside the flexible tube 1226, which, in turn, results in a decrease in stiffness (or increase in flexibility) of flexible tube 1226. This arrangement also affects the overall flexibility of insertion portion 1222, thus enabling control over its maneuverability inside a body cavity.

In embodiments, a pressure pump 1228 is connected to flexible tube 1226 at the proximal end of insertion portion 1222. In alternative embodiments, pressure pump 1228 is connected through the handle to flexible tube 1226. Pressure pump 1228 may control the pressure of water inside flexible tube 1226. Pressure control may be enabled through a button, a switch, or a knob located on the handle or on a main control unit of the endoscope assembly or by a foot pedal. The control may adjust the pressure by varying an operating voltage or by using a pressure regulator. In embodiments, water is input at an inlet 1230 of pump 1228. Water of variable pressure may be output through an outlet 1232, which feeds into flexible tube 1226. In embodiments, a user/physician interfaces with a scale that allows selection of a stiffness percentage, such as in the range of 0% to 100%. 0% may represent an insertion portion stiffness without any pressure, inside flexible tube 1226. And 100% may represent insertion portion 1222 with the maximum pressure that may be applied inside flexible tube 1226. A percentage value within this range may vary based on user requirements.

In alternative embodiments, other fluids may be used in place of water, within flexible tube 1226. Variable viscosity of a fluid may contribute to variation in stiffness of flexible tube 1226 containing the fluid. Therefore, any fluid that may change its viscosity properties may be used within flexible tube 1226. In embodiments, the fluid within flexible tube 1226 may undergo a viscosity change due to a change in at least one of temperature, electric charge, magnetic field, exposure to light, or any other factor influencing viscosity. Examples of such fluids may include, but are not limited to, electrorheological fluids that change viscosity based on an applied electric field, non-Newtonian fluids that change viscosity based on shear rate or shear rate history, magnetorheological fluids that change viscosity based on a magnetic field, photo-rheological fluids that change viscosity based on exposure to light, and the like.

In embodiments, electrorheological fluids (ERFs) are material composed of dielectric properties suspended in an insulating oil. Flow characteristics of ERFs may depend on properties of the dispersed material and the oil. Examples of ERFs include dispersions consisting of oil (mineral or silicon oil) and solid polymer particles, Hydroxyl-terminated silicon oil, RheOil®, and the like. In embodiments, magnetorheological fluids (MRFs) are liquids that display adjustable flow properties through introduction of magnetic fields. As a result, their characteristics can be changed from free flowing to solid and back again in a few milliseconds. Examples of MRF include fluid made using Carbonyl Iron powder, hydrocarbon-based MRFs, and the like.

In embodiments, pump 1228 is a lightweight pump suitable for liquids that provides a high-pressure capability for a small device. Pump 1228 may be a small-sized pump that delivers a consistent flow throughout a wide range of varying pressures. In embodiments, an electronic driver circuit may be used to operate the motor of pump 1228.

FIG. 12 also illustrates a horizontal cross sectional view of insertion portion 1222 above its longitudinal cross-sectional view. This view shows an exemplary position of flexible tube 1226 within insertion portion 1222. Flexible tube 1226 is seen positioned at the radial center of insertion portion 1222. Thus, flexible tube 1226 enables variation in flexibility of insertion portion 1222 from within and from its center. In another embodiment, flexible tube 1226 may be positioned in an empty space within and along insertion portion 1222. In embodiments, such empty spaces may include but are not limited to spaces between electronic wires, working channels, and air/water channel(s).

In an alternative embodiment, flexible tube 1226 is coiled around an outer circumferential surface of a treatment tool insertion channel, such as a working channel, embedded within insertion portion 1222. In this case, flexible tube 1226 coils around entire length of the working channel extending from the proximal end of insertion portion 1222. In another embodiment, flexible tube 1226 coils around the working channel and terminates some distance prior to the bending section of insertion portion 1222.

In yet another embodiment, flexible tube 1226 is replaced with a flexible lining that extends from a proximal end of insertion portion 1222 along length of insertion portion 1222. The flexible lining may form a tubular wall concentric to the inner wall of insertion portion 1222 such that a gap exists between the two walls. In embodiments, at least one flexible lining stretches along the inner wall of insertion portion 1222. In alternative embodiments, multiple flexible linings may be utilized. The flexible lining forms a parallel wall inside insertion portion 1222 such that a gap exists between the parallel wall and the inner wall of insertion portion 1222. A pressure pump may be connected to the gap at the proximal end of insertion portion 1222 that controls pressure of a fluid that fills the gap.

Figure 13A:
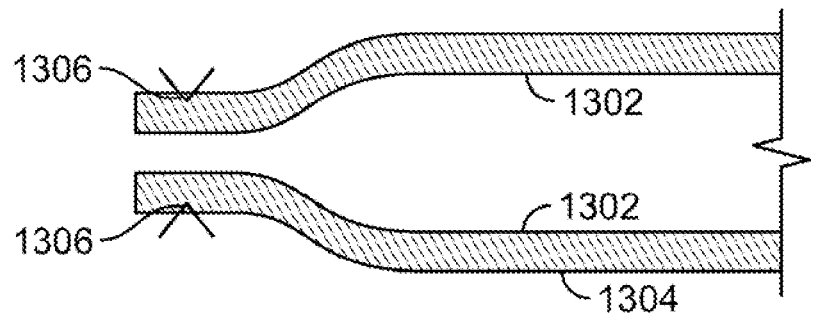
FIG. 13a illustrates an embodiment of a sealing mechanism used to seal a flexible lining within an insertion portion.

FIGS. 13*a*, 13*b*, 13*c*, and 13*d* illustrate various embodiments of methods that are utilized to seal the flexible lining. In embodiments, the flexible lining may be sealed at the distal end of insertion portion 1222. FIG. 13*a* illustrates a method of sealing by soldering a flexible lining 1302, with the wall of an insertion portion 1304 at its distal ends 1306. In embodiments, flexible lining 1302 may be punched at its distal ends with insertion portion 1304.

Figure 13B:
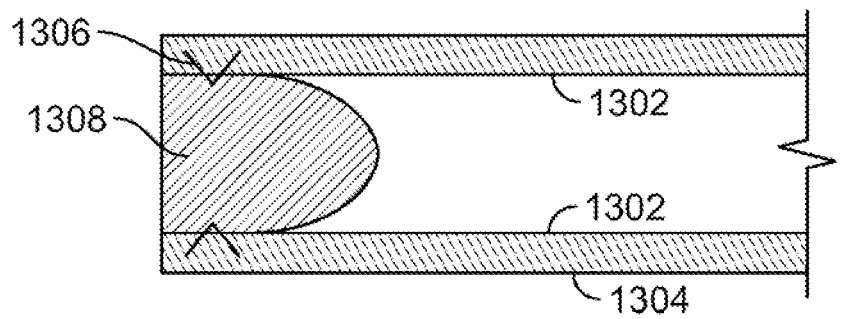
FIG. 13b illustrates another embodiment a sealing mechanism used to seal a flexible lining within an insertion portion.

FIG. 13*b* illustrates another embodiment where a plug 1308 is utilized in addition to sealing by soldering flexible lining 1302 with the wall of insertion portion 1304 at its distal ends 1306. Plug 1308 may be placed between inner walls of flexible lining 1302 proximal to ends 1306 to provide additional support to sealed ends 1306.

Figure 13C:
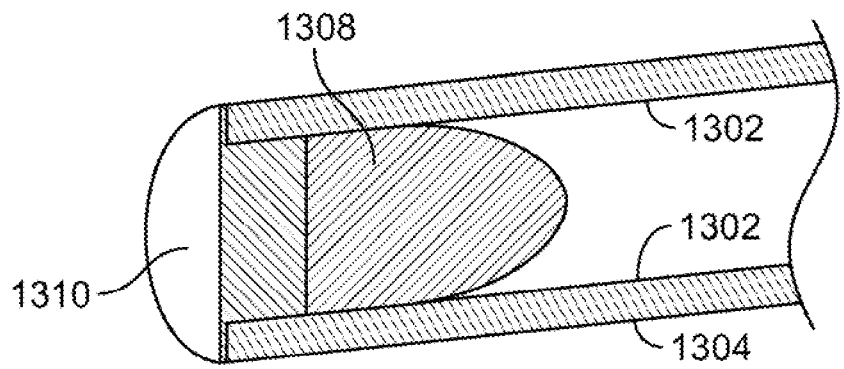
FIG. 13c illustrates another embodiment a sealing mechanism used to seal a flexible lining within an insertion portion.

FIG. 13*c* illustrates another embodiment where an Ultra Violet (UV) cure adhesive 1310 is used to seal open ends of flexible lining 1302, in addition to plug 1308.

Figure 13D:
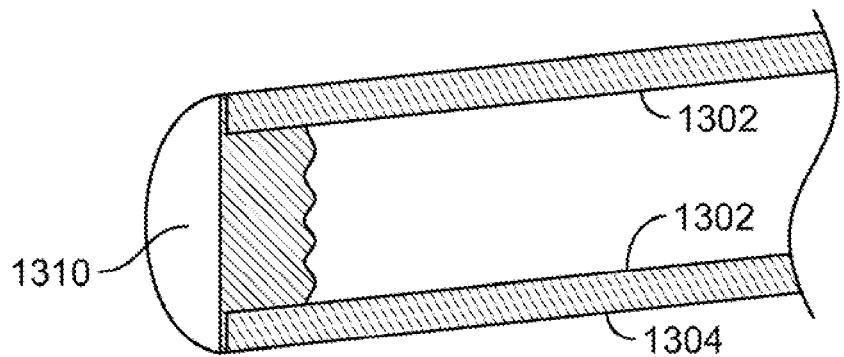
FIG. 13d illustrates another embodiment a sealing mechanism used to seal a flexible lining within an insertion portion.

FIG. 13*d* illustrates yet another embodiment where only UV cure adhesive 1310 is used to seal open ends of flexible lining 1302.

Figure 14:
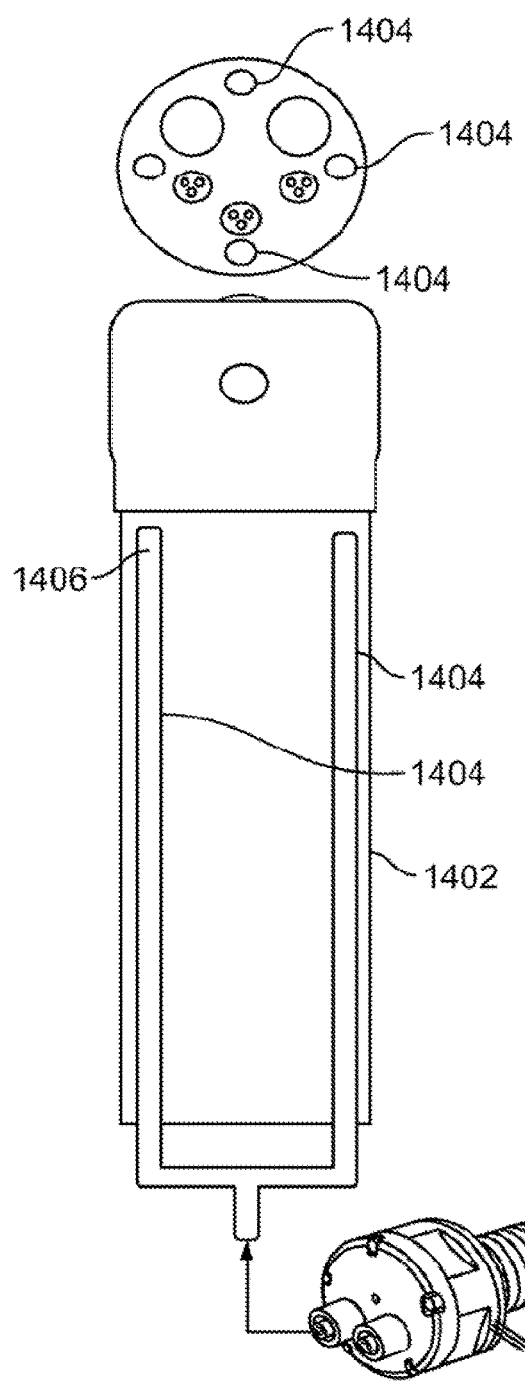
FIG. 14 shows a cross-sectional view of a portion of an elongated shaft in an endoscope in accordance with another embodiment.

FIG. 14 illustrates a cross-sectional view of another embodiment of an insertion portion 1402. In this embodiment, two or more flexible tubes 1404 are inserted within insertion portion 1402. Sealed ends 1406 towards the distal ends of each of tubes 1404 may seal the tubes, such that it carries a volume of water enclosed within tubes 1404.

An increase in this volume results directly in an increase of pressure of the water inside the flexible tubes 1404, which, in turn, results in an increase in stiffness (or decrease in flexibility) of flexible tubes 1404. Conversely, a decrease in this volume results directly in a decrease of pressure of the water inside the flexible tubes 1404, which, in turn, results in a decrease in stiffness (or increase in flexibility) of flexible tubes 1404. This arrangement also affects the overall flexibility of insertion portion 1402, thus enabling control over its maneuverability inside a body cavity.

Figure 15:
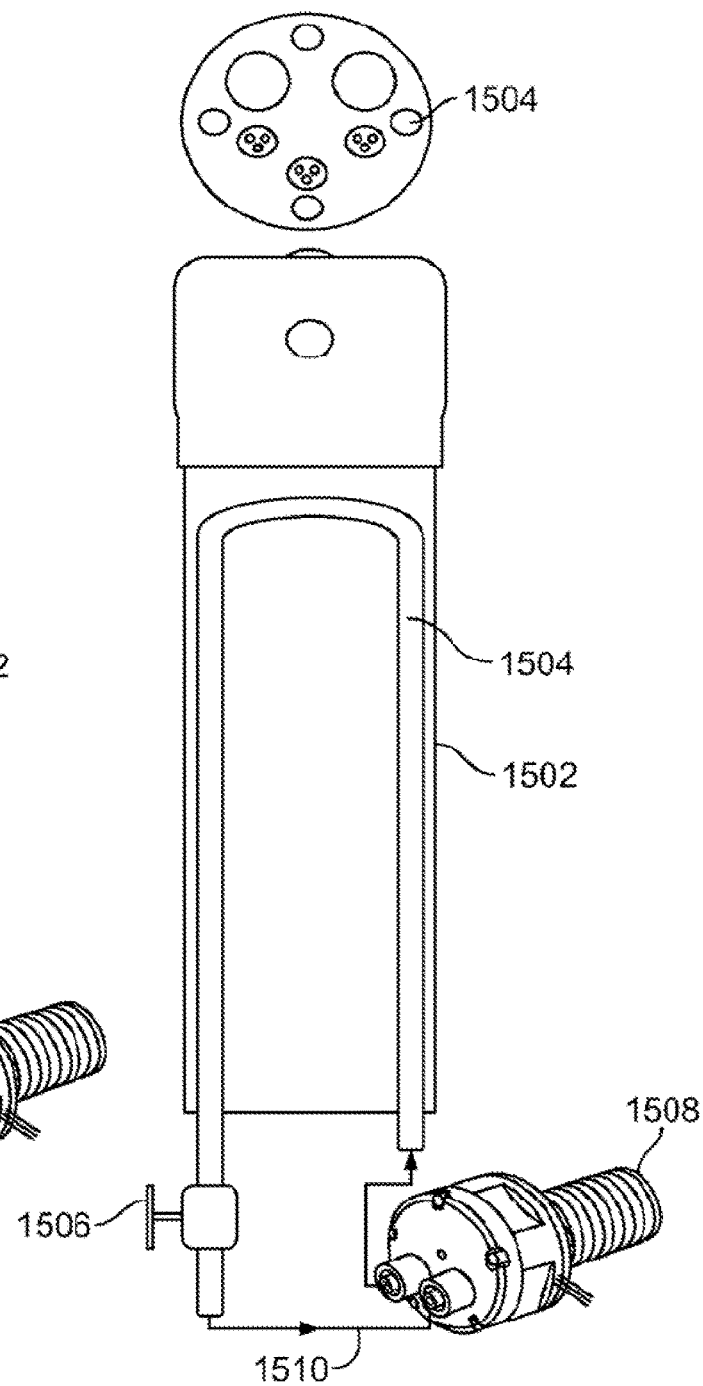
FIG. 15 shows a cross-sectional view of a portion of an elongated shaft in an endoscope in accordance with yet another embodiment.

FIG. 15 illustrates a cross-sectional view of yet another embodiment of an insertion portion 1502. In this embodiment, a flexible tube 1504 is inserted inside insertion portion 1502. Tube 1504 stretches along one side of an inner wall of insertion portion 1502, and may continually stretch along another side of the inner wall of insertion portion 1502. Tube 1504 may bend near the distal end of insertion portion 1502 to direct its water contents along other sides of its inner wall. In embodiments, flexible tube 1504 may be placed within insertion portion 1502 during its extrusion. In alternative embodiments, a guide is used to insert and place flexible tube 1504 inside insertion portion 1502. Once tube 1504 is placed, the guide may be withdrawn from insertion portion 1502.

FIG. 15 also illustrates a pressure-regulating valve 1506 that may be used to stop or allow the water within tube 1504 from flowing back to a pressure pump 1508 through an inlet 1510. In embodiments, once pressure-regulating valve 1506 is closed, water stops flowing out of tube 1504, such that a volume of water is enclosed within tube 1504. An increase or decrease in this volume results directly in an increase or decrease of pressure of the water inside tube 1504. An increase in this volume results directly in an increase of pressure of the water inside the flexible tube 1504, which, in turn, results in an increase in stiffness (or decrease in flexibility) of flexible tube 1504. Conversely, a decrease in this volume results directly in a decrease of pressure of the water inside the flexible tube 1504, which, in turn, results in a decrease in stiffness (or increase in flexibility) of flexible tube 1504. This arrangement also affects the overall flexibility of insertion portion 1502, thus enabling control over its maneuverability inside a body cavity.

FIGS. 16*a*, 16*b*, 16*c*, and 16*d* show longitudinal cross-sectional views of a portion of an elongated shaft in an endoscope in accordance with another embodiment. Referring to FIG. 16*a* to 16*d*, an insertion portion 1602 terminates at a tip section 1610 (shown in FIG. 16*a*), which is at the distal end of insertion portion 1602. In embodiments, at a proximal end, a handle (not shown) connected to insertion portion 1602 assists in maneuvering it within the body cavity. The arrangement of these components is described above with reference to FIG. 1.

Referring to FIG. 16*a*, in embodiments, a flexible tube 1604*a* extends from the proximal end of insertion portion 1602 along its length. The illustrated embodiment shows flexible tube 1604*a* terminating near tip section 1610. In alternative embodiments, flexible tube 1604*a* terminates within the bending section of insertion portion 1602. In another embodiment, flexible tube 1604*a* terminates some distance prior to the bending section of insertion portion 1602. In embodiments, flexible tube 1604*a* is configured to carry gas, such as but not limited to air, or fluid. In embodiments where gas/fluid inflates flexible tube 1604*a*, the gas/fluid may be sourced from the same supply that feeds the injector channel. Flexible tube 1604*a* may open into a sealed gas chamber 1612 near tip section 1610, such that the gas carried by tube 1604*a* is filled inside chamber 1612.

An increase or decrease in this volume of the gas within tube 1604*a* results directly in an increase or decrease of pressure of the gas within chamber 1612. An increase in this volume results directly in an increase of pressure of the gas within chamber 1612, which, in turn, results in an increase in stiffness (or decrease in flexibility) of insertion portion 1602 that houses chamber 1612. Conversely, a decrease in this volume results directly in a decrease of the pressure of the gas within chamber 1612, which, in turn, results in a decrease in stiffness (or increase in flexibility) of insertion portion 1602 that houses chamber 1612.

Referring to FIG. 16*b*, an additional flexible tube 1604*b* is shown. Flexible tube 1604*b* may be similar in its characteristics and operation to flexible tube 1604a, and may open into a different chamber 1614 (similar to chamber 1612). In embodiments, chamber 1614 may be located adjacent to chamber 1612 along the longitudinal axis of insertion portion 1602. In another embodiment, chamber 1614 is located at a predefined distance from chamber 1612 along the longitudinal axis of insertion portion 1602. Chambers 1612 and 1614 may be placed concentrically, such that chamber 1612 is inside chamber 1614, and both are aligned inside and along the inner circumferential surface of insertion portion 1602.

Referring to FIG. 16c, another flexible tube 1604c is shown. Flexible tube 1604c may be similar in its characteristics and operation to flexible tubes 1604a and 1604b, and may open into a third chamber 1616 (similar to chambers 1612 and 1614). In embodiments, chamber 1616 may be located adjacent to chamber 1614 along the longitudinal axis of insertion portion 1602. In an embodiment, chamber 1616 may be located at a predefined distance from chamber 1614 along the longitudinal axis of insertion portion 1602. Chambers 1612, 1614, and 1616 may be placed concentrically, such that chamber 1612 is inside chamber 1614, which is inside chamber 1616, and both all are aligned inside and along the inner circumferential surface of insertion portion 1602.

In embodiments, insertion portion 1602 may include multiple chambers, and the number of chambers may vary. Length of chambers may also vary. In an embodiment, length of the chambers may vary from 1 to 30 cm. In other embodiments, the lengths may exceed 30 cm.

Pressure of gas/fluid may be varied separately in all of the chambers described in the above embodiments to variably control stiffness of insertion portion 1602.

In embodiments, a pressure pump 1608 is connected to flexible tubes 1604a, 1604b, and 1604c, at the proximal end of insertion portion 1602. In alternative embodiments, pressure pump 1608 is connected through the handle. Pressure pump 1608 may control pressure of gas inside each flexible tube 1604a, 1604b, and 1604c. A switch 1606 or any other external control (such as a button or a knob) may enable an operator to configure pressures within each tube and thus each chamber, to manage stiffness of insertion portion 1602. Switch 1606 may be located on the handle or on a main control unit of the endoscope assembly. The control may adjust the pressure by varying an operating voltage or through a pressure regulator.

Various embodiments of the specification described herein may thus allow flexibility of an insertion portion of an endoscope to vary, thereby increasing ease of navigation through different parts and contours inside a body cavity while solving problems related to looping. The gas and fluid pressure controls provide an additional layer of control over the flexibility of the insertion portion of most available endoscopes.

Alternative embodiments may also be considered that enable control over the flexibility of the insertion portion. These additional alternatives may be in the form of various methods of manufacturing the insertion tube of the insertion portion. Such embodiments enable flexibility of the insertion tube to be controlled on the basis of the manufactured characteristics of the tube. Some embodiments of methods of manufacturing are discussed here.

Immersion Method

The immersion method of manufacturing the insertion tube may enable control over rigidity of different areas of the tube. Rigidity of the tube may be controlled by use of different viscosity liquids that construct the base material of a jacket of the tube, which is also known as a sheath. In embodiments, the jacket may be Thermoplastic Polyurethane. Additionally, a portion of the sheath may be of the braided hose type. In embodiments, the hose braid may be manufactured using stainless steel, or a synthetic material, or Kevlar, or any other material known in the art. In embodiments, the type of hose braid used (wire diameter, number of wires per bobbin, number of carriers) also affects the rigidity of the tube. Moreover, flat coils may be used as framework for insertion tubes to provide control over the rigidity of the tube. In embodiments, flat coils may be manufactured using stainless steel, or copper, or any other material known to manufacture flat coils. An advantage of the immersion method is that the insertion tubes manufactured by this method do not require an extra coating.

Extrusion Method

This method offers advantages when the control over stiffness of the insertion tube is maintained with hose braids and flat spirals. One of the advantages include an improved quality of connection of the insertion tube with its mesh, which is used for the jacket. The improved quality of connection ensure that the sheath remains attached to the tube braid, and thus a widespread form of beads bend in the insertion tube in a tight radius. With a surface treatment of the tubular braid and/or use by the extrusion, a uniform thickness of the casing is achieved. This also results in improved uniformity of stiffness in the rigidity zones. Another advantage is that insertion tubes have a constant stiffness among different manufacturing batches. As a result, the reject rate in production by this method is much lower. Additionally, the tubes manufactured by this method may have a relatively smoother surface. The insertion tubes manufactured by this method also do not require an extra coating.

Shrink Tube Method

In this method, flat coils are prepared with the hose braid, and coated with a heat shrink tube, followed by baking in an oven until maximum shrinkage is reached. Variable stiffness may be achieved with this method by differing the quality of the flat coils and of the hose braid.

Various embodiments of the specification described herein may thus allow flexibility of an insertion portion of an endoscope to vary, thereby increasing ease of navigation through different parts and contours inside a body cavity while solving problems related to looping.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method of tensioning an insertion portion of a medical device,
   wherein the medical device comprises:
   (1) a handle connected to the insertion portion at a proximal portion of the insertion portion,
   (2) a bending portion at a distal portion of the insertion portion, and
   (3) an actuator,
   the method comprising:
   actuating the actuator; and activating a spring to deform the spring, wherein a proximal portion of the spring is connected to a wire extending along a length of the insertion portion, wherein a distal end of the wire is connected to the bending portion such that the wire is pulled when the spring is deformed, wherein a shaft connects the spring to the wire, wherein the shaft has a U-shaped structure comprising:
a first wall connected to a distal end of the spring; and
a second wall, parallel to the first wall, connected to a proximal end of the wire.

2. The method of claim 1, wherein the proximal portion of the spring is connected to the actuator.

3. The method of claim 1, wherein the spring comprises superelastic material.

4. The method of claim 3, wherein the superelastic material is Nitinol.

5. The method of claim 1, wherein activating the spring includes providing an electric current source to the spring.

6. The method of claim 1, wherein activating the spring includes providing a heat source to the spring.

7. The method of claim 1, wherein the actuator is connected to a gear motor.

8. The method of claim 1, wherein the wire is inside a coil fixed to an internal periphery of the insertion portion.

9. The method of claim 1, wherein a housing contains at least one of the actuator, the spring, and the wire.

10. The method of claim 9, wherein a proximalmost end of the wire is received in the housing.

11. The method of claim 1, wherein the handle includes a steering actuator, and the method further comprises:
actuating the steering actuator to deflect the bending portion, wherein the proximal end of the wire terminates at a position distal to the steering actuator.

12. The method of claim 1, wherein the insertion portion includes (i) a working channel and (ii) an enforcement layer over an exterior of the working channel configured to increase stiffness of the insertion portion.

13. A method of tensioning an insertion portion of a medical device,
wherein the medical device comprises:
(1) the insertion portion,
(2) a bending portion at a distal portion of the insertion portion, and
(3) an actuator,
the method comprising:
actuating the actuator;
activating a spring to deform the spring, wherein a proximal portion of the spring is connected to a wire extending along a length of the insertion portion, wherein a distal end of the wire is connected to the bending portion such that the wire is pulled when the spring is deformed, and
displaying a degree of stiffness of the insertion portion on an electronic display.

14. The method of claim 13, wherein activating the spring includes at least one of modifying a pitch, a length, a degree of compression, or a degree of expansion of the spring.

15. The method of claim 13, wherein the spring includes one of a tension/extension spring, a compression spring, a constant spring, a variable spring, a coil spring, a flat spring, and a machined spring.

16. The method of claim 13, wherein the spring includes a tube comprising a plurality of slits extending in a longitudinal direction along walls of the tube.

17. The method of claim 13, wherein the medical device further comprises an external control configured to actuate bending of the bending portion, and
the method further comprising actuating the external control to bend the bending portion.

18. A method of tensioning an insertion portion of a medical device,
wherein the medical device comprises:
(1) the insertion portion,
(2) a bending portion at a distal portion of the insertion portion, and
(3) an actuator,
the method comprising:
actuating the actuator; and
activating an elastically deformable member to deform the elastically deformable member, wherein a proximal portion of the elastically deformable member is connected to a wire extending along a length of the insertion portion, wherein a distal end of the wire is connected to the bending portion such that the wire is pulled when the elastically deformable member is deformed, wherein a shaft connects the elastically deformable member to the wire,
wherein the shaft has a U-shaped structure comprising:
a first wall connected to a distal end of the elastically deformable member; and
a second wall, parallel to the first wall, connected to the proximal end of the wire.

19. The method of claim 18, wherein the proximal portion of the elastically deformable member is connected to the actuator.

20. The method of claim 18, wherein the elastically deformable member comprises superelastic material.

21. The method of claim 18, wherein the wire is inside a coil fixed to an internal periphery of the insertion portion.

* * * * *